(12) United States Patent
Kwak et al.

(10) Patent No.: US 11,643,634 B2
(45) Date of Patent: May 9, 2023

(54) METHOD OF PREPARING POLYVINYL ALCOHOL NANOFIBER MEMBRANE ENHANCING CELL SPECIFIC ADHESION

(71) Applicant: NANOFAENTECH CO., LTD., Gimhae-si (KR)

(72) Inventors: Jong-Young Kwak, Suwon-si (KR); Minho Choi, Seoul (KR); Gwang Lee, Suwon-si (KR)

(73) Assignee: NANOFAENTECH CO., LTD., Gimhae-si (KR)

( * ) Notice: Subject to any disclaimer, the term of this patent is extended or adjusted under 35 U.S.C. 154(b) by 513 days.

(21) Appl. No.: 16/803,957

(22) Filed: Feb. 27, 2020

(65) Prior Publication Data
US 2020/0283725 A1     Sep. 10, 2020

(30) Foreign Application Priority Data
Mar. 5, 2019   (KR) .................. 10-2019-0025279

(51) Int. Cl.
*B82Y 5/00*   (2011.01)
*B82Y 40/00*  (2011.01)
*B82Y 30/00*  (2011.01)
*C12N 5/00*   (2006.01)
*D01D 5/00*   (2006.01)
*D01F 6/14*   (2006.01)

(52) U.S. Cl.
CPC ........... *C12N 5/0068* (2013.01); *D01D 5/003* (2013.01); *D01F 6/14* (2013.01); *B82Y 5/00* (2013.01); *B82Y 30/00* (2013.01); *B82Y 40/00* (2013.01); *C12N 2533/30* (2013.01); *C12N 2533/50* (2013.01); *C12N 2537/10* (2013.01)

(58) Field of Classification Search
CPC .............. C12N 5/0068; C12N 2533/30; C12N 2533/50; C12N 2537/10; B82Y 30/00; B82Y 40/00
See application file for complete search history.

(56) References Cited

U.S. PATENT DOCUMENTS

2020/0239851 A1*   7/2020   Kwak ................. C12N 5/0671

FOREIGN PATENT DOCUMENTS

KR      10-1665918 B1     10/2016
WO    WO-2019059702 A2 *  3/2019 ........... C12N 5/0062

OTHER PUBLICATIONS

Chen et al., "Nanofibrous modification on ultra-thin poly(ε-caprolactone) membrane via electrospinning", Materials Science and Engineering: C, vol. 27, Issue 2, Mar. 2007, pp. 325-332 (Year: 2007).*
Park et al., "Surface hydrolysis of fibrous poly(ε-caprolactone) scaffolds for enhanced osteoblast adhesion and proliferation", Macromol. Res. 15, 424-429 (2007) (Year: 2007).*

* cited by examiner

*Primary Examiner* — Ruth A Davis
(74) *Attorney, Agent, or Firm* — Revolution IP, PLLC

(57) ABSTRACT

A method of preparing a polyvinyl alcohol nanofiber membrane includes a material for controlling cell specific adhesion, and a nanofiber membrane that can maintain cellular functions such as cell activity and growth is prepared by adding aqueous solutions containing a polyacrylic acid and a glutaraldehyde crosslinking agent in a polyvinyl alcohol and materials capable of enhancing or regulating cell adhesion, electrospinning, treating with hydrochloric acid vapor and dimethylformaldehyde solvent and treating with sodium hydroxide to control the cell adhesion.

6 Claims, 26 Drawing Sheets

METHOD OF PREPARING POLYVINYL ALCOHOL NANOFIBER MEMBRANE ENHANCING CELL SPECIFIC ADHESION

CROSS-REFERENCE TO RELATED APPLICATION

This application claims priority to and the benefit of Korean Patent Application No. 10-2019-0025279 filed in the Korean Intellectual Property Office on Mar. 5, 2019, the entire contents of which are incorporated herein by reference.

BACKGROUND OF THE DISCLOSURE

1. Field of the Disclosure

The present invention relates to a method of preparing a polyvinyl alcohol (PVA) nanofiber membrane for cell culture comprising a material capable of enhancing specific adhesion according to the type of cells, and more specifically, to a method of preparing a PVA nanofiber membrane for extracellular matrix and tissue microenvironment-like cell culture having the structural characteristics and the cell adhesion of the nanofiber.

2. Description of the Related Art

Conventional cell culture methods are two-dimensional and based on culturing cells while maintaining the adhesive property of cells in a polystyrene culture dish. Cells in living tissues grow or differentiate under a three-dimensional environment by extracellular matrix (ECM), and so two-dimensional culture has an extracellular environment different from that of living tissues. In order to overcome these limitations of two-dimensional cell culture, a three-dimensional cell culture method that is biomimetic and can improve cell culture efficiency has been developed. Recently, the importance of nanofibers as a three-dimensional cell culture support has been emerged, and nanofibers produced by electrospinning can be used as a promising support for tissue engineering applications because they are structurally similar to natural ECM.

PVA may be developed as a biomaterial of a biocompatible polymer, but due to its high hydrophilicity, cell adhesion is very low, so there is a limit to use as a material for cell culture. The nanofibers produced by electrospinning have a similar form to the ECM, but they also cross-link the PVA to increase the water resistance of the nanofibers made of PVA. Representative methods of crosslinking include chemical crosslinking using a crosslinking agent. Because bioactive materials must be uniformly dissolved in the electrospinning solution for electrospinning, and therefore, PVA, which is a water-soluble polymer, is most suitable as a support containing a water-soluble bioactive material such as protein or peptide. However, PVA has a disadvantage of poor cell adhesion due to high solubility in water and low protein affinity. For this reason, there is a need in the field of cell culture for the technique of the production of functional PVA nanofiber membranes that can maintain cell activity similar to that in tissues while maintaining the hydrophilicity of the PVA material itself as a transparent PVA nanofiber support that is insoluble in water.

Extracellular matrix is composed of an aggregate of biopolymers that create an extracellular environment as well as play a physiological and chemical role in addition to a physical role to fill the gap between cells. The major component of the ECM is collagen and collagen fibers are intercellularly connected by cell-adhesive proteins such as fibronectin and laminin, etc. Arg-Gly-Asp (RGD) peptide is peptide sequences found mainly in fibronectin and are important sites for cell binding and is the major integrin binding domain present in extracellular such as vitronectin, fibrinogen and osteopontin. Laminin imparts cell adhesion as a major component of the basal lamina to which epithelial cells adhere in the basement membrane. Representative cell binding site of laminin is the Tyr-Ile-Gly-Ser-Arg sequence (peptide YIGSR) of the B1 chain, RGD sequence in the laminin protein also corresponds to the cell binding site. Nanofibers containing such cell-adhesive proteins or peptides can provide an environment of ECM similar to the human body.

Protein may be denatured or lost activity due to glutaraldehyde which is a chemical crosslinking agent added during the nanofiber manufacturing process. In most cases, cell-adhesive proteins or peptides are coated on nanofibers or culture plates to enhance cell adhesion. Techniques produced by electrospinning with laminin in ε-polycaprolactone polymer dissolved in fluoroalcohol without using a crosslinking agent are introduced. Polymers such as keratose which is keratin component and chitosan are known to be easily fabricated as nanofibers by electrospinning with PVA. Nanofibers produced by electrospinning a peptide-PVA polymer solution without mixing a crosslinking agent may be utilized as a drug secretion support by using a phenomenon in which peptide secretion is gradually increased. Compared to this technique, a method of adding a drug to the PVA polymer solution and treating the nanofibers with glutaraldehyde vapor after electrospinning is used to increase the degree of crosslinking and prevent drug release. The release of peptides mixed in PVA nanofibers with or without crosslinking agents can be assumed to be caused by the chemical property of hydrophilicity or physical property of PVA dissolving in water. Therefore, the bioactive material has a problem of being released from highly hydrophilic PVA nanofibers and thus it is necessary to develop a technology that can overcome these technical limitations.

SUMMARY OF THE DISCLOSURE

An object of the present invention is to provide a method for preparing a PVA nanofiber membrane having enhanced cell adhesion, which comprises a material capable of controlling cell adhesion and function while securing transparency, water resistance and hydrophilicity of PVA nanofibers; a PVA nanofiber membrane having enhanced specific adhesion to various types of cells prepared by the method; and a three-dimensional cell culture method with enhanced cell adhesion using the PVA nanofiber membrane.

In order to achieve the above object, the present invention provides a method of preparing PVA nanofiber membrane having enhanced cell adhesion, comprising: (1) preparing PVA nanofiber membrane by adding cell-adhesive material to an electrospinning solution containing PVA, polyacrylic acid (PAA) and glutaraldehyde (GA) and electrospinning; (2) cross-linking the PVA nanofiber membrane by hydrochloric acid (HCl) vapor treatment, followed by crystallization by treating with dimethylformamide (DMF) solvent; and (3) treating crystallized PVA nanofiber membrane with sodium hydroxide.

In addition, the present invention provides a PVA nanofiber membrane with enhanced cell adhesion prepared by the above method.

In addition, the present invention provides a three-dimensional cell culture method with enhanced cell adhesion comprising three-dimensionally culturing cells in the PVA nanofiber membrane.

DETAILED DESCRIPTION OF THE EMBODIMENTS

Figure 1:
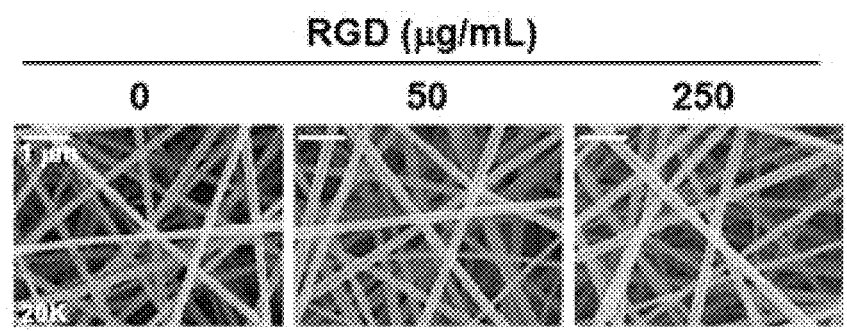
FIG. 1 is an electron microscope image confirming the shape and degree of voids of peptide Arg-Gly-Asp (RGD)-containing nanofiber membrane consisting of three amino acids Arginine, Glycine and Aspartate by electrospinning according to the present invention.

Accordingly, the present inventors have made efforts to solve the problem of deterioration of cell adhesion when PVA nanofibers are prepared by adding a chemical cross-linking agent and thus prepared a PVA nanofiber support containing a cell binding specific peptide or ligand and devised a method of completely releasing a substance in an aqueous solution by weakly binding to nanofibers, and completed the technique to simulate ECM similar to a living microenvironment that can provide a culture environment with increased binding capacity of cells cultured by a ligand attached to nanofibers.

Namely, the present inventors used a combination of chemical crosslinking agents capable of maintaining the transparency of the PVA nanofiber membrane and prepared nanofibers containing bioactive modulators such as peptides and the like. This process is simple and easy to manufacture and thus it is possible to culture various types of cells and can significantly reduce the cost of culture. In addition, nanofibers prepared by blending various types of cellular active materials can provide a three-dimensional ECM environment suitable for the cells to be cultured. In particular, the present invention has excellent efficacy in culturing epithelial cells with poor cell adhesion and can provide a support capable of three-dimensional culture and maintaining the function of cultured cells without inducing epithelial-mesenchymal transition due to the adhesion of epithelial cells to culture dish.

The present invention provides a method of preparing PVA nanofiber membrane having enhanced cell adhesion, comprising: (1) preparing PVA nanofiber membrane by adding cell-adhesive material to an electrospinning solution containing PVA, polyacrylic acid (PAA) and glutaraldehyde (GA) and electrospinning; (2) cross-linking the PVA nanofiber membrane by hydrochloric acid (HCl) vapor treatment, followed by crystallization by treating with dimethylformamide (DMF) solvent; and (3) treating crystallized PVA nanofiber membrane with sodium hydroxide.

Preferably, the cell-adhesive material may be a cell-binding peptide or fucoidan and more preferably, the cell-binding peptide may be RGD peptides, KGRGDS peptides, GGPEILDVPST peptides or YIGSR peptides, but it is not limited thereto.

Preferably, the cell may be epithelial cells, vascular epithelial cells, cancer cells, fibroblasts, hepatocytes, immune cells or stromal cells, but it is not limited thereto.

Preferably, the cell-binding peptide may be added at a concentration of 10 to 300 µg/mL, but it is not limited thereto.

Preferably, the fucoidan may be added at a concentration of 1 to 20 mg/mL, but it is not limited thereto.

The PVA nanofiber membrane containing cell-adhesive material according to the present invention may have a role of enhancing cell adhesion, and cell function regulation includes various cellular functions such as viability, differentiation and activity and the like.

The PVA nanofiber membrane can be prepared by mixing cell adhesion factors, particularly peptides so as to improve adhesion of cells to the PVA nanofiber membrane, but they are not limited thereto and may include various kinds of proteins or peptides involved in the cell adhesion. It can be prepared by further mixing specific ligands for activity control in addition to cell adhesion depending on the type of cells.

On the other hand, the method of preparing PVA nanofiber membrane having an enhanced cell-specific adhesion of the present invention is characterized in that a material for controlling cell activity such as peptides in the crystallized PVA nanofiber membrane is rapidly released by treatment with sodium hydroxide.

In addition, after a step of releasing a material for controlling cell adhesion, the cells may be cultured in a PVA nanofiber membrane including the material for controlling cell adhesion remaining without being released to the polyvinyl alcohol nanofiber membrane.

In addition, the material for controlling cell adhesion may be exposed on the surface of the PVA nanofiber membrane prepared through the blending of the material for controlling cell adhesion such as peptides to bind to the receptors of the cell surface.

The PVA nanofiber membrane comprising the cell-adhesive material according to the present invention can rather inhibit the cell binding capacity when the cells are cultured without sodium hydroxide treatment and can be a condition that the cell activity is affected by the secreted material.

In addition, the present invention provides a PVA nanofiber membrane with enhanced cell adhesion prepared by the preparation method In addition, the present invention provides a three-dimensional cell culture method with enhanced cell adhesion comprising three-dimensionally culturing cells in the PVA nanofiber membrane.

Preferably, the cells may be epithelial cells, vascular epithelial cells, cancer cells, fibroblasts, hepatocytes, immune cells or stromal cells, but they are not limited thereto.

When the primary hepatocytes are cultured using the PVA nanofiber membrane comprising the cell-adhesive material of the present invention, the hepatocytes cultured for a long time by controlling the adhesion of the primary hepatocytes provides condition capable being cultured in the form of a spheroid or a single cell layer.

When immune cells are cultured using the PVA nanofiber membrane comprising the cell-adhesive material of the present invention, the cultured immune cells can provide condition that differs in cell activity by adhesion.

An analytical method capable of measuring the effects of drugs or irradiation on cell adhesion can be provide by using the three-dimensional cell culture system using the PVA nanofiber membrane comprising the cell-adhesive material of the present invention.

Hereinafter, examples of the present invention will be described in detail to understand the present invention. The following examples of the present invention are intended to embody the present invention, but not to limit the scope of the present invention. Therefore, what can be easily inferred by those skilled in the art to which the present invention pertains from the detailed description and the examples of this invention is interpreted as the scope of the present invention.

Reference Example 1

Preparation of PVA Nanofiber for Three-Dimensional Cell Culture

The PVA nanofibers for three-dimensional cell culture were prepared according to the method of Korean Patent No. 1665918. These PVA nanofibers are stable in water and transparent and have various degrees of cell adhesion depending on cell types and have an average diameter of 100-200 nm.

The electrospinning solution was prepared by dissolving polyvinyl alcohol (PVA, Mw=89,000-98,000, Sigma) and polyacrylic acid (PAA, Mw=2000, Sigma) in distilled water as a solvent to be concentration of 10% (w/v) and 0.2% (w/v), respectively, at 85° C. for 24 hours using a heating magnetic stirrer. The dissolved PVA solution was cooled completely at room temperature, and then mixed with glutaraldehyde (GA) for 2 minutes (v/v) for 30 minutes to prepare an electrospinning solution. Electrospinning solution of 4 mL was electrospun at 10 kV using two 27 G metal syringes at a distance of 10 cm at a rate of 8 μl/min. PVA/PAA/GA nanofibers prepared by electrospinning were heat-treated at 60° C. for 1 minute. In order to crosslink the nanofibers, nanofibers and hydrochloric acid (HCl) were added to a vacuum desiccator and treated with hydrochloric acid vapor for 60 seconds in a vacuum state. The nanofibers treated with hydrochloric acid vapor were treated with dimethylformamide (DMF) solution for 1 minute and then completely dried, soaked in distilled water for 3 hours and sterilized by exposure to ultraviolet light for 12 hours. The nanofiber membrane thus produced exhibits characteristics that do not undergo gelling even when treated in distilled water, while maintaining transparency.

Example 1

Preparation of PVA Nanofibers Blended with Cellular Active Materials

RGD-PVA nanofiber membrane was prepared by performing an electrospinning process, hydrochloric acid vapor treatment, and solvent treatment in the substantially same manner as the method of preparing a nanofiber membrane except for adding RGD to a PVA/PAA/GA solution as an electrospinning solution. PVA and PAA were added to distilled water, and materials for controlling cell activity such as peptides, fluorescein sodium salt and fucoidan were mixed and dissolved at 85° C. for 24 hours using a heating magnetic stirrer, followed by addition of glutaraldehyde and electrospinning of the prepared solution to prepare nanofibers. Nanofiber membranes were prepared to have a thickness of 50-60 μm. During the process of dissolving PVA and PAA, heat is applied for a long time, and thus proteins weak in heat may be added with glutaraldehyde after cooling the PVA/PAA solution. After electrospinning, the treatment with hydrochloric acid vapor and dimethylformamide were performed in the same manner as in Reference Example 1.

The surface structure of the PVA nanofiber support blended with the PVA nanofiber support prepared in Reference Example 1 and Example 1 was confirmed using a scanning electron microscope (SEM). For observation using an electron microscope, SNE-4500M (Sec, Korea) was used as a scanning electron microscope after the nanofibers were coated with platinum. Referring to FIG. 1, the fibers constituting the PVA nanofiber support containing 50 μg/mL or 250 μg/mL RGD peptide through the electrospinning process, as confirmed by the electron microscopy images, have no beads and have a constant diameter of 180-300 nanometers (220±60 nm).

Example 2

Evaluation of Cell Adhesion in RGD-PVA Membrane

Nanofiber membranes were attached to 8 well culture plates and cells were seeded onto the nanofiber membranes. However, the attachment of the membrane is not limited to 8 wells and plates or transwells having various sizes may be used. Plates to which the membrane is attached were sterilized in an ultraviolet box filled with 70% ethanol (1 mL) for at least 18 hours. After removing ethanol from it, it was filled with the cell culture medium (1 mL) and put in a $CO_2$ incubator at 37° C. and soaked 12 hours for the use.

CT-26 colorectal cancer cells, NIH3T3 fibroblasts, EA.hy926 vascular endothelial cells (ATCC, Manassas, Va., USA) were cultured in Dulbecco's Modified Eagle's Medium (DMEM) medium containing FBS (10%), penicillin (100 IU/mL) and streptomycin (100 μg/mL) and MLE-12 cells, which are mouse airway epithelial cells, were purchased from ATCC and the cells were cultured in an incubator maintained at 5% $CO_2$ concentration at 37° C. using DMEM/F-12 high glucose culture solution containing FBS (10%) and penicillin (100 IU/mL). CT-26, NIH3T3, EA.hy926 and MLE-12 cells were stained with PKH26 red fluorescence (Sigma) and then cultured using the culture solution at $3 \times 10^4$ cells/700 μL/1 $cm^2$ per well on a nanofiber membrane.

Figure 2:
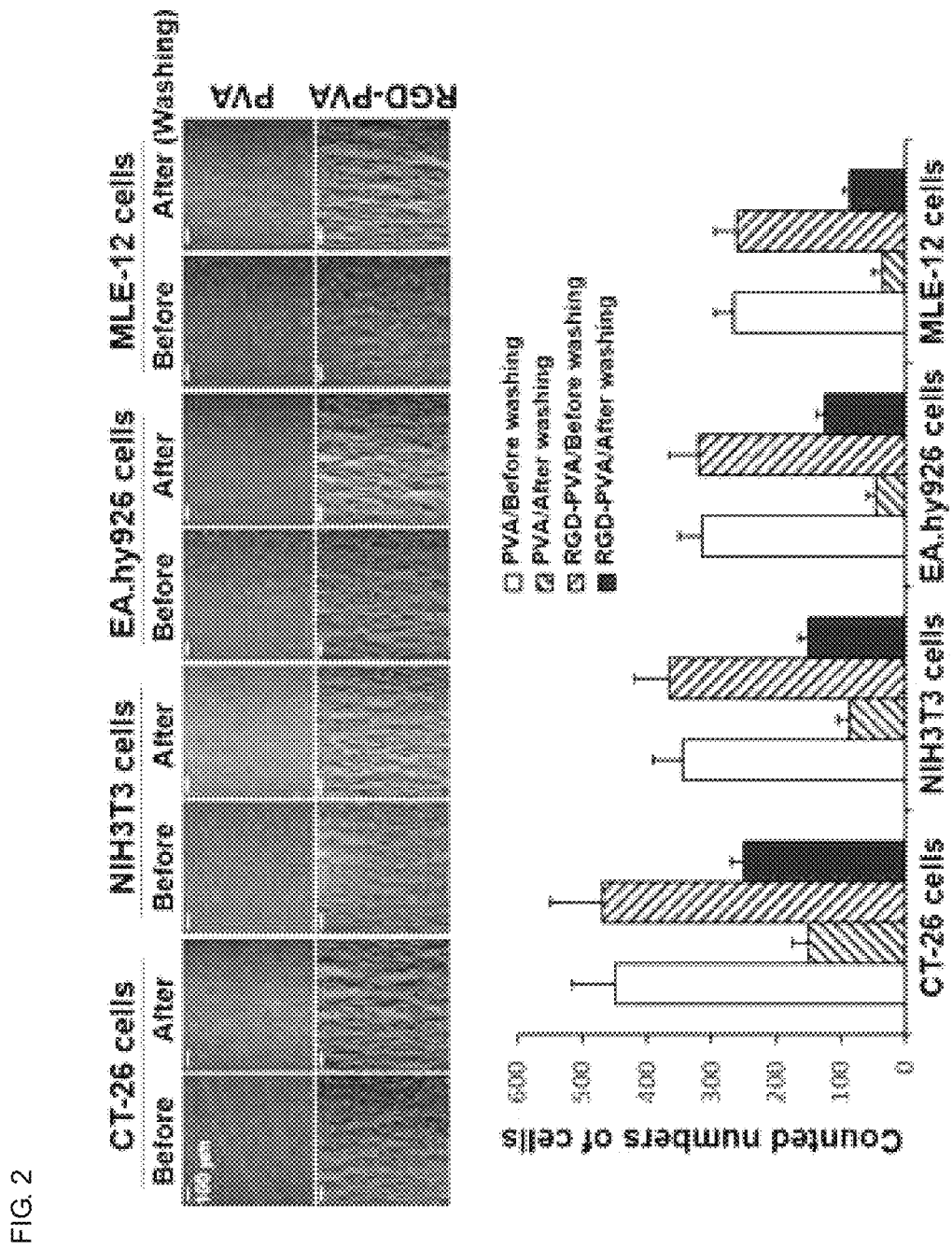
FIG. 2 shows a result of measuring the number of fluorescence stained cells by differential interference contrast (DIC) microscope and confocal fluorescence microscope of cells adhered to RGD-containing nanofiber membranes before and after washing with culture medium after culturing fluorescently stained cells stained on RGD-containing nanofiber membranes according to the present invention.

According to Example 1 of the present invention, RGD-PVA membrane containing RGD (50 μg/mL) in a nanofiber spinning solution and PVA membrane without RGD were prepared, and cells with different adherence were seeded on these membranes for 4 hours and then the number of cells attached to the surface was measured. As shown in FIG. 2, in a short time, the number of colorectal cancer cells adhered to the nanofibrous membrane was higher than epithelial cells. Cell adhesion in PVA nanofibers containing RGD did not increase significantly compared to that in PVA membrane. The cells were seeded on PVA and RGD-PVA nanofiber membranes, and after 4 hours, the cells were shaken at a speed of 50×rpm for 45 minutes in a shaker, and then the number of cells attached to the nanofibers was measured after removing unbound cells by washing away. "Before" is a mixed image of confocal microscope and differential interference microscope before washing the nanofiber membrane to which cells are attached, and "After" is a mixed image after washing. After washing, cells of all kinds were remarkably detached and the adhesion of MLE-12 cells was the lowest. In addition, the number of cells adhered relatively well, such as CT26 and NIH3T3, after washing on the RGD-PVA membrane was found to be larger than that on the PVA membrane, but a large number of cells were washed off and detached from the RGD-PVA.

Example 3

Measurement of Fluorescence Leakage in PVA Nanofibers Containing Fluorescence Sodium Salt In order to measure the degree of secretion of the material mixed in the PVA solution, a fluorescent-PVA nanofiber was prepared by mixing the fluorescent material. The dissolved PVA solution was completely cooled at room temperature, and then mixed with green fluorescence sodium salt (Sigma) at a concentration of 100 µg/mL for 24 hours using a magnetic stirrer. Glutaraldehyde of 2% (v/v) was added and mixed for 30 minutes to prepare an electrospinning solution and the solution was electrospun to produce a fluorescent nanofiber membrane. After the process was the same as the PVA nanofiber preparation method.

Figure 3:
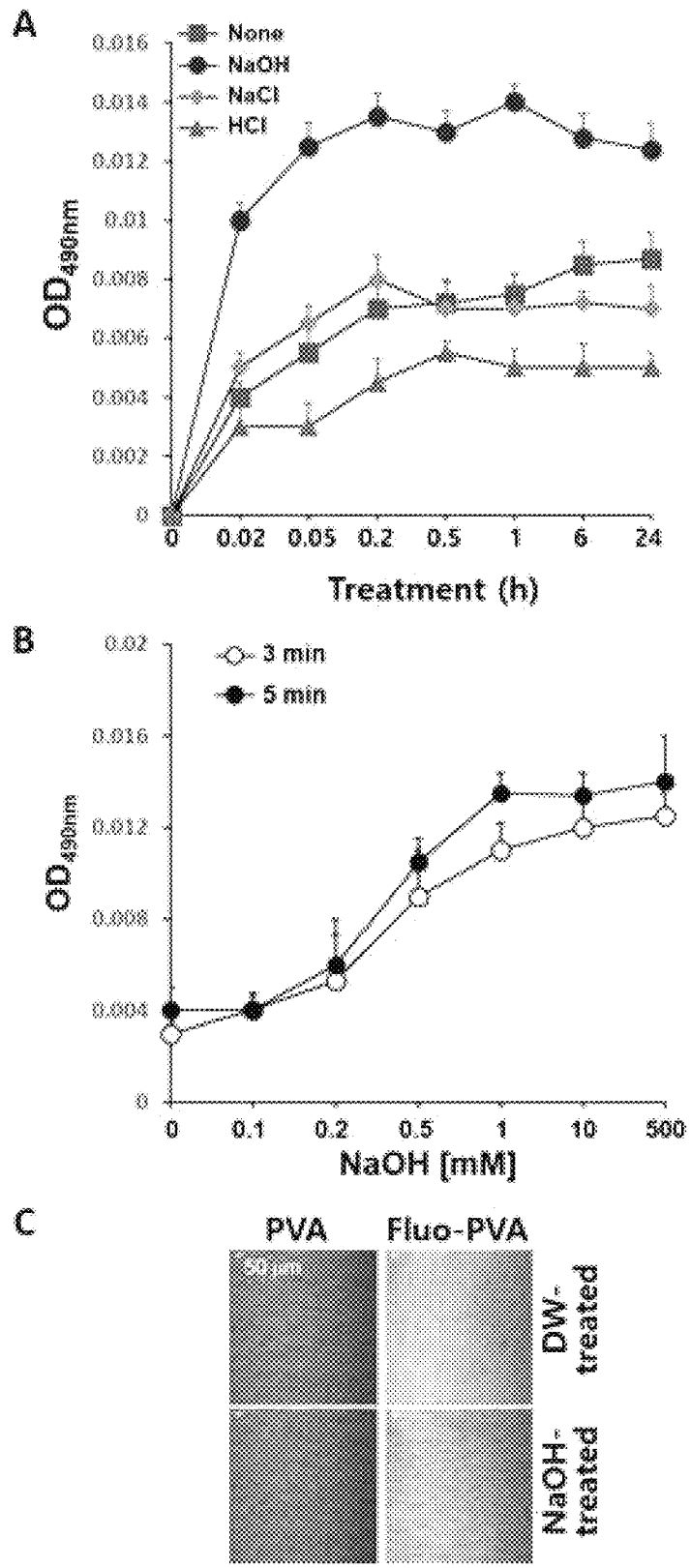
FIG. 3 shows a result of measuring the fluorescence dissolved in the solution after immersing nanofibers containing fluorescence sodium salt in distilled water or 1M sodium hydroxide solution over time and the result of observing the fluorescence remaining in the nanofibers by the confocal fluorescence microscope.

In order to confirm the degree of fluorescence leakage, the membrane was immersed in distilled water and the concentration of fluorescence material dissolved in distilled water released from the nanofiber was measured. FIG. 3 is a result of measuring the fluorescence dissolved in the solution after immersing the nanofibers containing fluorescence in water or 1 M sodium hydroxide solution at 490 nm. FIG. 3A shows that the amount of fluorescence in the aqueous solution flowed out from the nanofibers immersed in distilled water was small and the amount of fluorescence was gradually increased, but in the case of nanofibers immersed in various concentrations of sodium hydroxide solution, it was confirmed that a high degree of fluorescence in the solution was measured in a very short time. Compared with these results, the outflow of the substance contained in the nanofibers by the salt of 1M sodium chloride (NaCl) or strong acid such as 1M hydrochloric acid (HCl) was much lower than that of sodium hydroxide. The concentration of fluorescence outflow in the sodium hydroxide solution did not increase further after 1 hour of reaction. When immersed in distilled water, the fluorescent material was continuously released up to 48 hours. Therefore, these results suggest that water-soluble compounds that are weakly bound to highly hydrophilic PVA nanofibers can be released as water-soluble compounds and that the outflow occurs rapidly by alkaline treatment such as sodium hydroxide. As shown in FIG. 3B, as the concentration of sodium hydroxide increased, the fluorescent salts contained in the electrospinning solution were released from the nanofibers.

FIG. 3C is a result confirming whether the fluorescent material remains in the PVA nanofibers other than the fluorescent material released from the PVA nanofibers treated with sodium hydroxide. PVA nanofibers containing fluorescent salts were treated with sodium hydroxide and distilled water for 24 hours, dried and observed by confocal microscopy and the nanofiber membranes showed fluorescence, which was much lower than that treated with sodium hydroxide. Therefore, it was confirmed that all substances weakly bound to the nanofibers were released by treating with sodium hydroxide and the fluorescence bound to the nanofibers is confirmed to remain by further treatment. Accordingly, the present invention provides a method of preparing a membrane to which a substance added to nanofibers can be stably attached by treatment with sodium hydroxide.

Example 4

Figure 4:
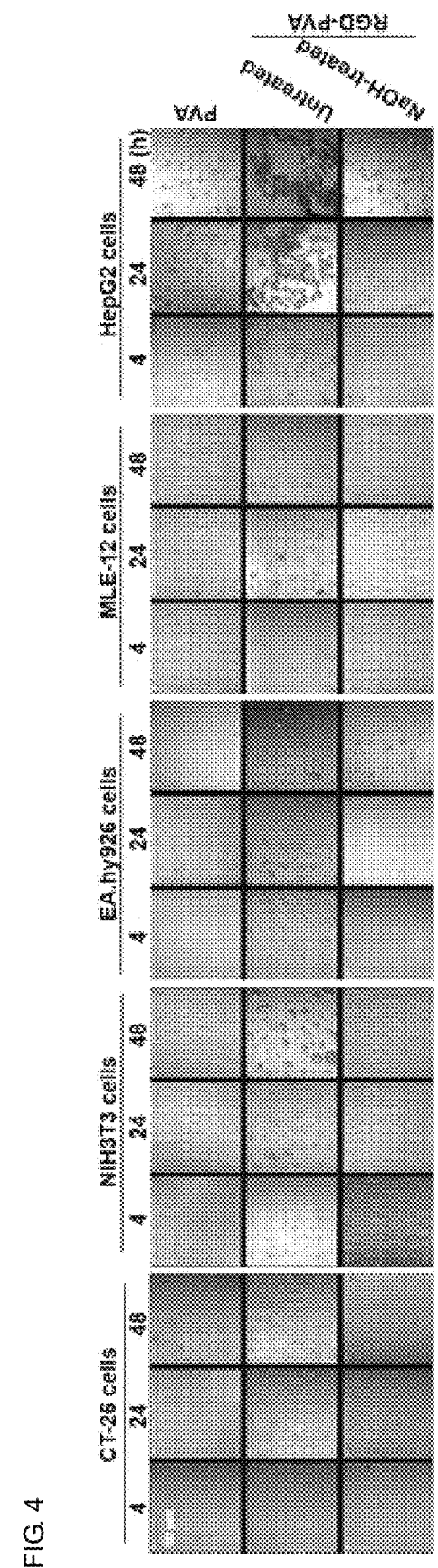
FIG. 4 shows images of measuring a degree of adhesion and cell growth patterns when fluorescence stained cells were incubated on PVA nanofibers, RGD-containing nanofibers (untreated) and RGD-containing nanofibers treated with sodium hydroxide (NaOH-treated) membranes according to the present invention for 48 hours by the confocal microscope and the differential interference microscope.

Comparative Measurement of Adhesion and Growth of Cells on RGD-Containing PVA Membranes with or without Treatment of Sodium Hydroxide It was determined whether the cell adhesion was increased by culturing cells to the nanofiber-bound RGD remaining on the RGD-PVA membrane treated with sodium hydroxide. NIH3T3 fibroblasts, CT-26 colorectal cancer cells, HepG2 hepatocarcinoma cells, EA.hy926 vascular endothelial cells and MLE-12 airway epithelial cells were stained with PKH26, a red fluorescent substance, followed the dispensation of the cells at $3 \times 10^4$ to a PVA membrane and an RGD-PVA membrane without treatment of sodium hydroxide, and RGD-PVA membrane after treatment with 1 M sodium hydroxide for 1 hour and washing (hereinafter referred to as RGD-NaOH-PVA). After 4 hours, 24 hours and 48 hours of culture, the growth patterns of the cells were measured by confocal microscopy and shown in FIG. 4. Compared to the PVA membrane, the aggregation of cells cultured in RGD-PVA without treatment of sodium hydroxide was further increased, especially HepG2 cell culture showed the highest aggregation. In comparison, cells cultured on RGD-PVA membrane treated with sodium hydroxide showed no aggregation and the cells were uniformly distributed.

Figure 5:
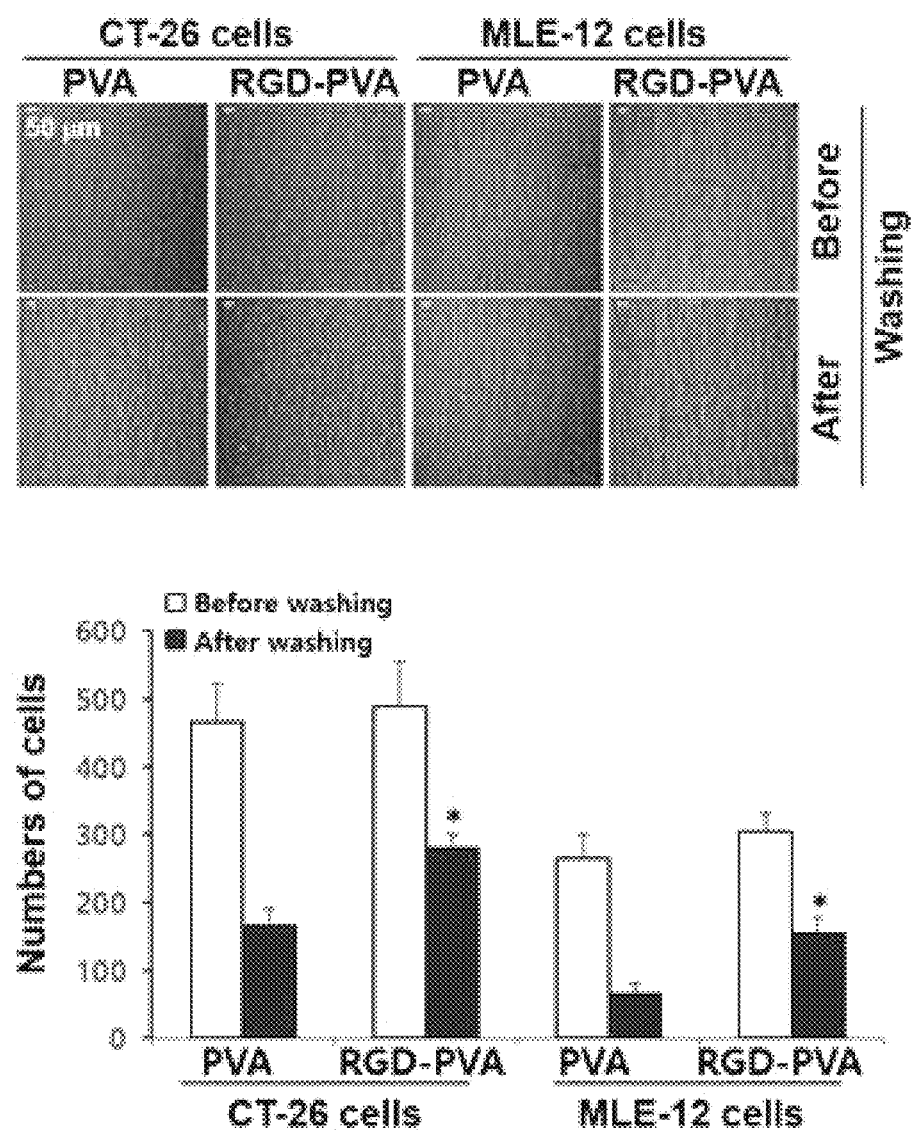
FIG. 5 shows a result of measuring the number of remaining cells before and after washing cells to compare the adhesion of two types of cells cultured on RGD-PVA membrane treated with sodium hydroxide by the confocal microscope.
Figure 6:
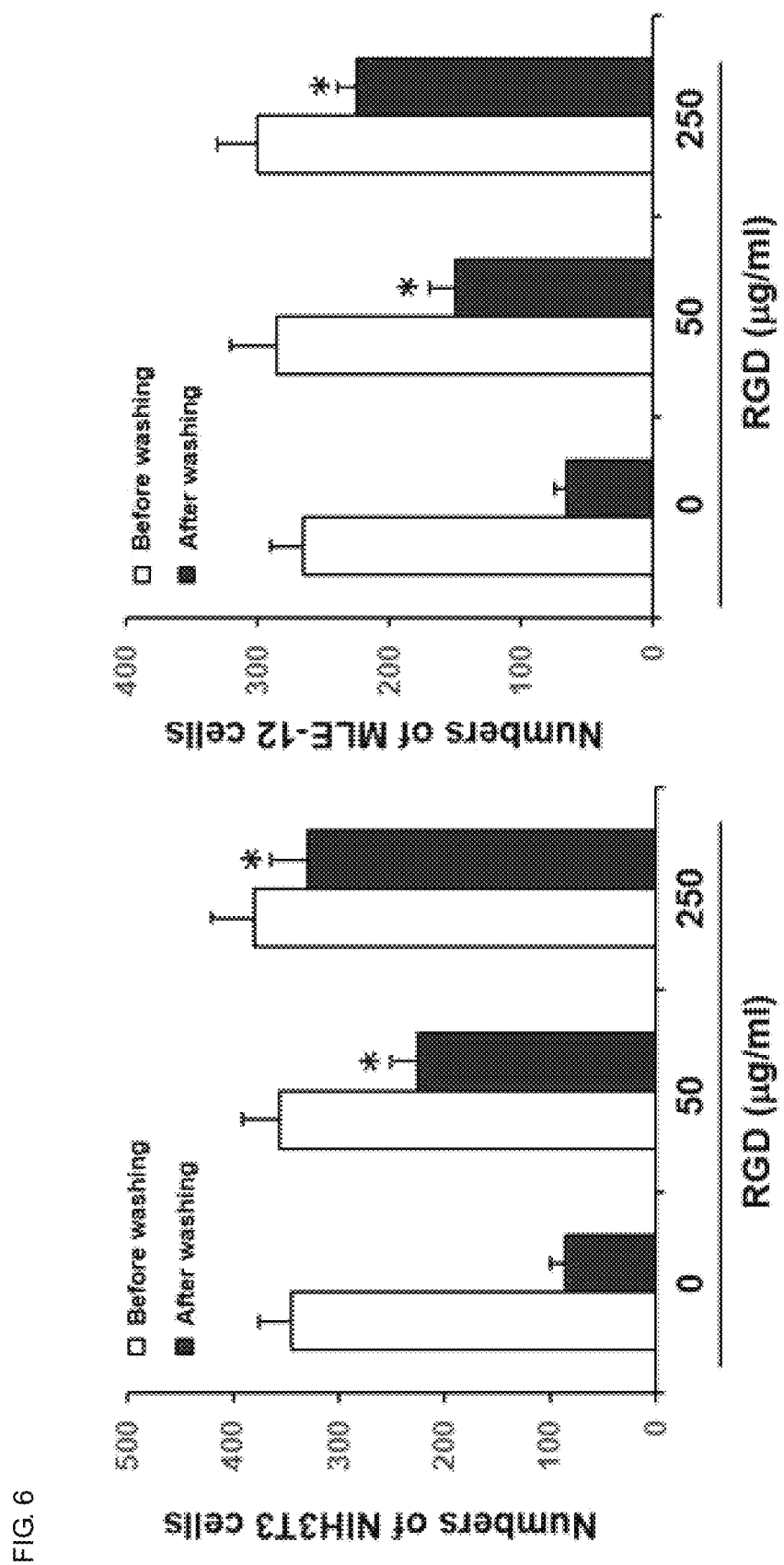
FIG. 6 shows a result of measuring the number of attached cells after the RGD-PVA membrane containing various concentrations of RGD, which is treated with sodium hydroxide followed by adhesion of the cells into membranes containing different concentrations of RGD and washing with the culture medium.

Cell adhesion ability in PVA nanofibers containing RGD did not increase significantly compared to that in PVA membranes, moreover, the number of cells attached to nanofibers after washing did not increase significantly. As shown in FIG. 5, CT-26 cancer cells and MLE-12 epithelial cells having different surface adhesion were seeded on the RGD-NaOH-PVA membrane and the number of the cells attached even after washing with the culture solution was found to be more than in the PVA membrane. In particular, the adhesion of cancer cells to RGD-NaOH-PVA membrane was higher than that of epithelial cells. As shown in FIG. 6, as the concentration of RGD contained in the PVA nanofibers increased, the adhesion of NIH3T3 and MLE-12 cells washed after seeding on the RGD-NaOH-PVA membrane was increased.

Figure 7:
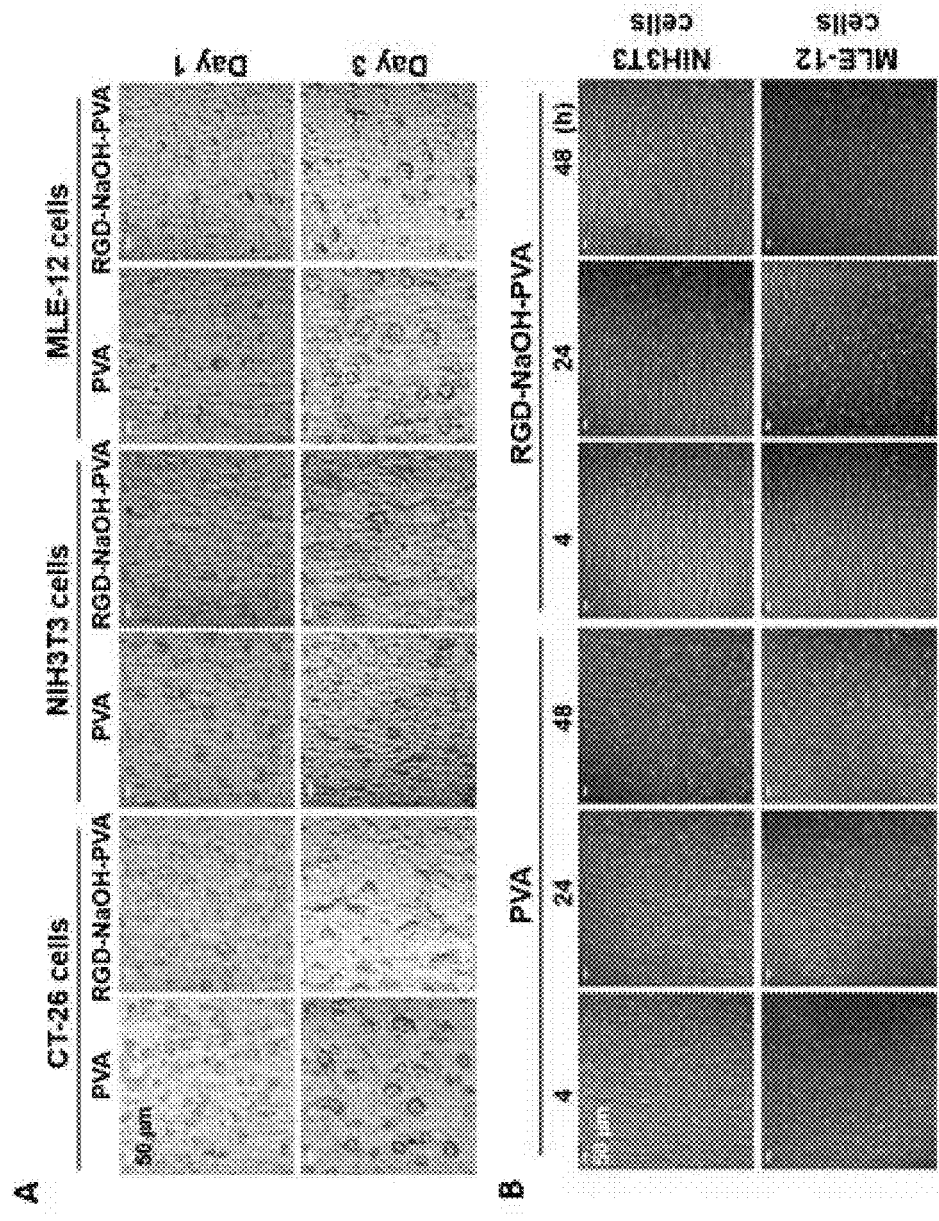
FIG. 7 shows differential interference photographs measured by the confocal microscope (FIG. 7A) and results of observing the growth and adhesion patterns of the fluorescently stained cells by the fluorescence microscope (FIG. 7B) to describe the adhesion patterns and characteristics of cells cultured on RGD-PVA membrane treated with sodium hydroxide.

Since the PVA membrane has transparency, the growth of cells can be measured by observing the morphology of cells cultured in a general culture dish. As shown in FIG. 7, CT-26 colorectal cancer cells or NIH3T3 fibroblasts among the cells cultured on the RGD-NaOH-PVA membrane grow in a more stretched shape due to increased adhesion compared to cells cultured on the PVA membrane. The MLE-12 airway epithelial cells showed the adhesion characteristics of the cells since the cells aggregated and grown even on RGD-NaOH-PVA. This pattern was shown to be similar when the cells stained with PKH26 were cultured and measured by confocal microscopy.

Figure 8:
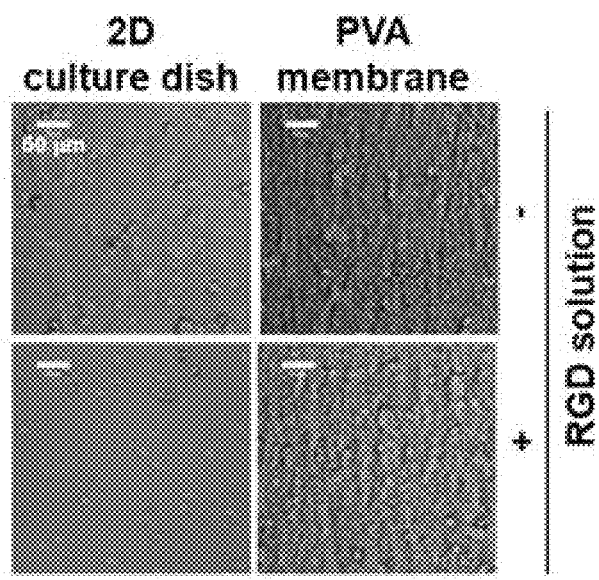
FIG. 8 shows a result of antagonistic inhibition by the confocal microscope whether the increase in adhesion of cells cultured on RGD-containing nanofiber membrane (PVA membrane) prepared according to Example 1 of the present invention is suppressed by the RGD (RGD solution) added to the culture medium compared to 2D culture dish.

Next, it was determined whether the adhesion of cells cultured on the RGD-NaOH-PVA membrane was increased due to RGD. As shown in FIG. 8, RGD (250 ng/ml) was added to the cell culture solution to observe cell adhesion after 24 hours. Cells cultured in commonly used culture dishes showed a decrease in cell number due to decreased adhesion, and the attached cells also had a circular shape. MLE-12 cells cultured on the PVA membrane showed a decrease in cell number, while increased cell aggregation by treatment with RGD. These results suggest that although laminin is primarily involved in are primarily involved in the attachment of epithelial cells to the basement membrane, the cell binding of fibronectin is also involved in the adhesion of these cells.

Example 5

Measurement of Immunofluorescence Staining of MLE-12 Epithelial Cells Cultured on RGD-NaOH-PVA Membrane As for MLE-12 airway epithelial cells, the tight junction between cells are well formed in two-dimensional culture. The adhesion pattern and the degree of cell tight junction of MLE-12 airway epithelial cells cultured on RGD-NaOH-PVA membrane were compared and analyzed under confocal microscope. MLE-12 cells ($3 \times 10^4$/700 µL/cm$^2$) were dispensed under different conditions and incubated for 1, 3 and 5 days in an incubator maintained at 5% $CO_2$ and 37° C. and fixed for 10 min with 4% PFA at room temperature. After washing three times with PBS for 5 minutes, it was treated with PBST (PBS containing 0.1% Triton X-100) containing 5% goat serum for 1 hour and reacted with the primary antibody at 4° C. for 24 hours. Zona occludens-1 (ZO-1), an antibody for confirming intercellular tight junction was diluted at a ratio of 1:100 and phalloidin was diluted at a ratio of 1:200 and they were reacted for 24 hours and washed three times with PBS for 10 minutes. As a secondary antibody, Alexa Fluor® 488 and Alexa Fluor® 594 were diluted at a ratio of 1:200, respectively and added to the samples, and reacted at room temperature for 1 hour. The sample was washed with PBS for 5 minutes and then diluted with DAPI in a ratio of 1:1000 and reacted for 10 minutes. Samples were encapsulated using a mounting gel and observed using a confocal microscope.

Figure 9:
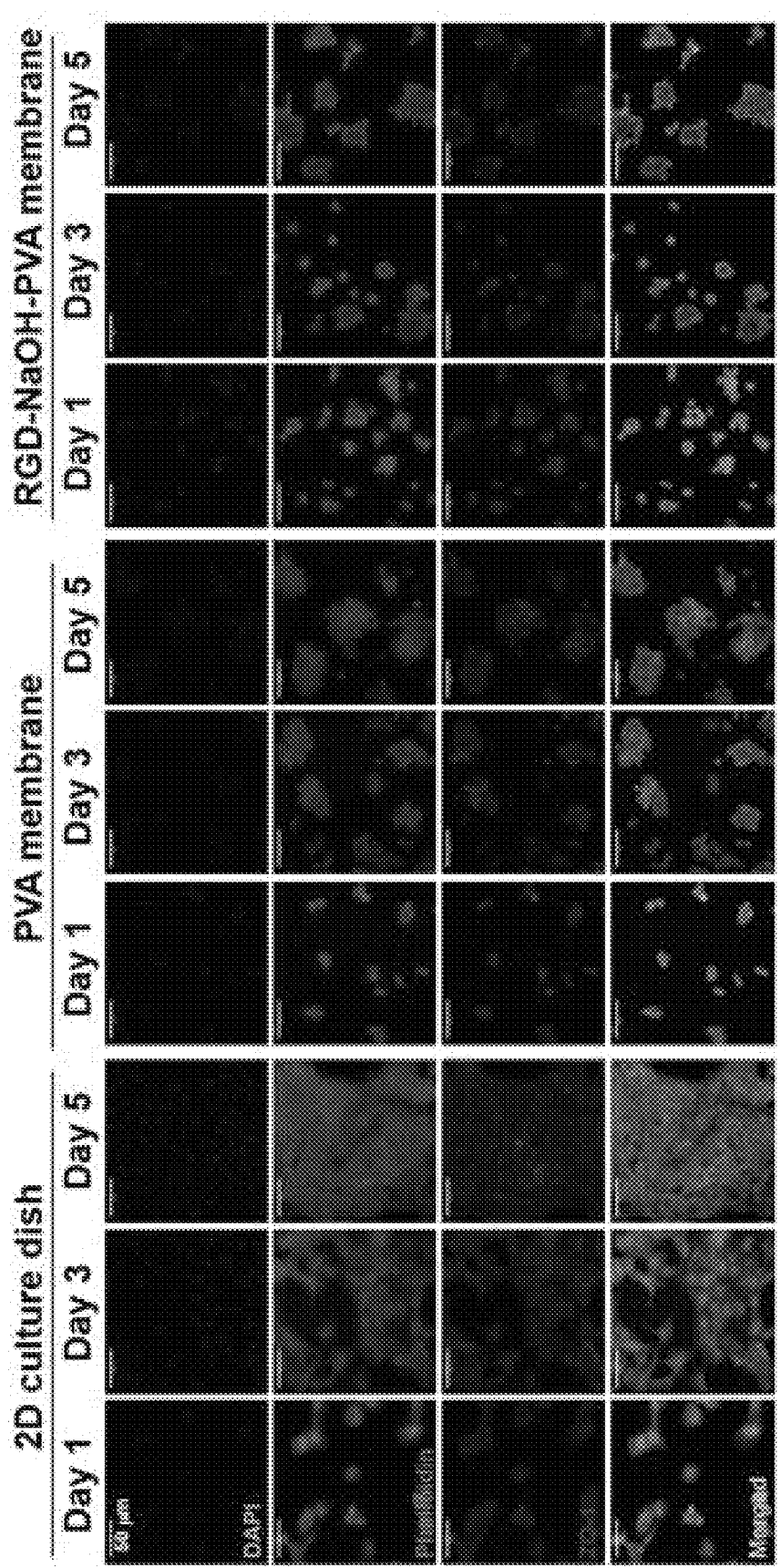
FIG. 9 shows a result of the adhesion patterns and the degree of cell junction of MLE-12 airway epithelial cells cultured on RGD-containing PVA membrane treated with sodium hydroxide by the confocal microscope.

As shown in FIG. 9, the cells cultured on the PVA membrane do not undergo strong cell adhesion as in the culture dish. When cells were dispensed on the PVA membrane and cultured for 24 hours, MLE-12 cells had decreased adhesion and aggregated between cells and until 3 days after the culture, the expression of ZO-1, a protein involved in cell tight junction, was unclear but after 5 days of culture, the cells was aggregated and showed a significant increase in the expression of ZO-1 on the surface thereof. This phenomenon occurred similarly in RGD-PVA not treated with sodium hydroxide, but the degree of cell aggregation was not larger than that of cells cultured on PVA membrane and formed as small aggregates. In comparison, MLE-12 cells cultured in RGD-NaOH-PVA did not significantly increase cell aggregation and the intercellular tight junctions occurred. MLE-12 cells cultured in the culture dish as a control showed a very high bonding between cells due to the high proliferation and strong adhesion to the surface of the culture dish.

Example 6

Figure 10:
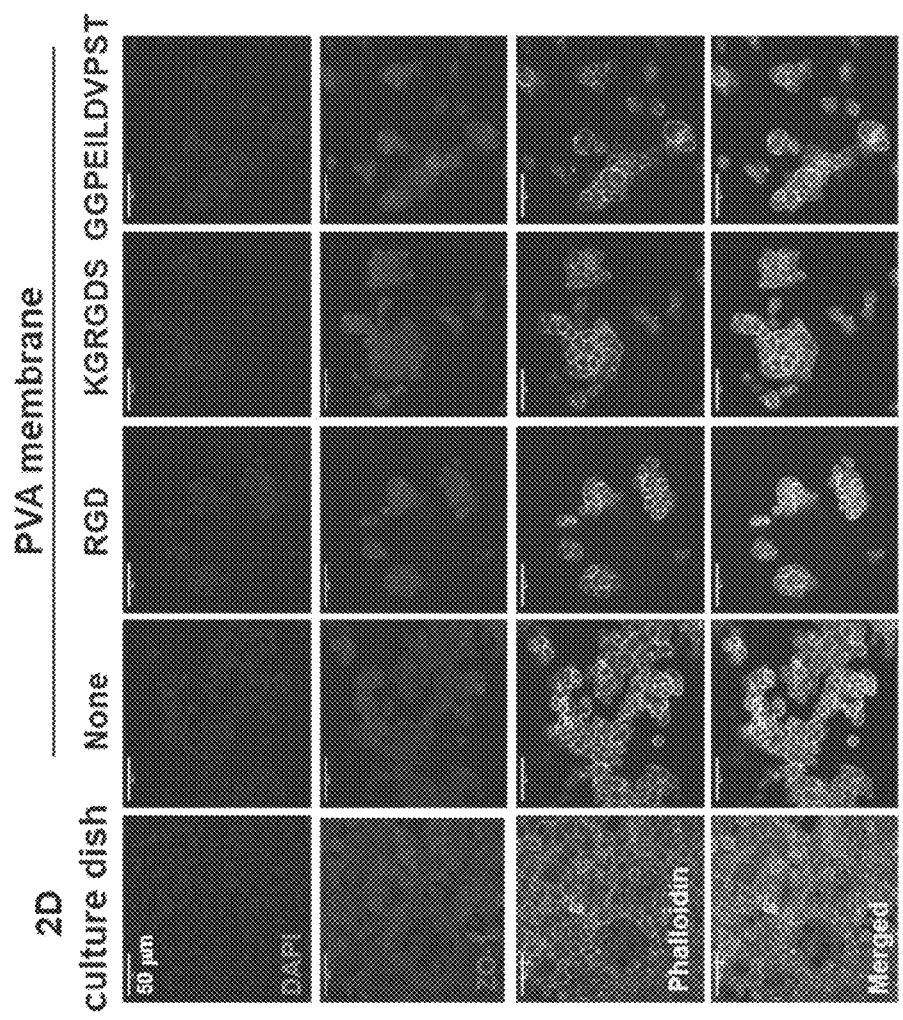
FIG. 10 shows a result of measuring the adhesion and the degree of cell junction of cells cultured on these membranes after preparing PVA membrane containing peptide KGRGDS and peptide GGPEILDVPST and treating with sodium hydroxide as compared to PVA membrane containing RGD peptide by the confocal microscope.

Measurement of Adhesion Property of Cells Cultured on PVA Membrane Containing Cell Binding Peptides Other than RGD PVA membrane containing RGD peptide as well as peptide KGRGDS which is a cell binding site of fibronectin, and peptide GGPEILDVPST containing another cell binding site were added to PVA solution at a concentration of 50 µg/mL and PVA membranes containing these peptides prepared by electrospinning were treated with sodium hydroxide, and five days after the culture of airway epithelial cells in these membranes, the degree of adhesion and cell tight junction were analyzed for comparison. As shown in FIG. 10, the cell aggregation was highest in the PVA membrane without the fibronectin peptide, and the cells cultured in the PVA membrane containing the KGRGDS peptide or the GGPEILDVPST peptide, as in the RGD-PVA, showed no aggregation. Therefore, the cell adhesion enhancing effect was obtained not only in RGD but also in PVA membranes containing other types of peptides corresponding to the cell binding domain of fibronectin.

Epithelial cells cultured on the PVA membrane increased the expression of protein having cell tight junction at the site of intercellular contact by cell aggregation, but there is a problem that the cell proliferation was so low that the cultured cells were not uniformly distributed in the nanofibers. It can be solved by a peptide-containing nanofiber to enhance cell adhesion.

Example 7

Figure 11:
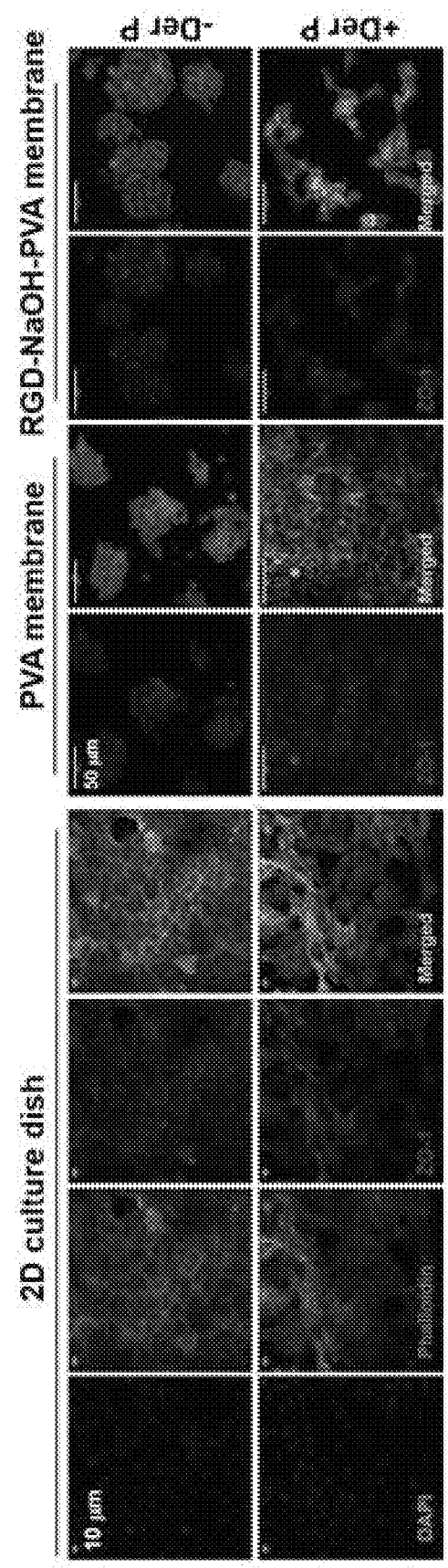
FIG. 11 shows a result of examining the effect of asthma-inducing allergen (Der P) on cell adhesion and growth in the culture dish and PVA membranes by staining with antibodies to actin and ZO-1 protein by the confocal microscope.

Evaluation of Allergen Effect on Airway Epithelial Cell Adhesion in RGD-PVA Membrane Treated with Sodium Hydroxide The effect of Der P, a component of house dust mite, an allergen that causes asthma, on airway epithelial cells was compared in two and three dimensional cultures. As shown in FIG. 11, cells treated with Der P in a two dimensional culture dish for 5 days showed a significant increase in actin expression in order to maintain cell adhesion to the surface of the dish in the weakness of cell tight junction. However, airway epithelial cells cultured on the PVA membrane to which Der P was added for 5 days exhibited that only the expression of ZO-1 which forms the cell tight junction, was lost while maintaining the cell morphology, but the expression of actin was not significantly increased. In comparison, the cells cultured on the RGD-NaOH-PVA membrane showed a significant increase in the expression of actin as well as the loss of cell tight junction as in the two dimensional culture dish and accordingly, it is suggested that the phenomenon depends on the culture state.

Example 8

Evaluation of Adhesion and Activity of Immune Cells in PVA Membrane

When bone marrow-derived dendritic cells (BMDCs) are cultured in culture dishes or polycaprolactone nanofibers, unstimulated cells are not activated state and the addition of the activating material causes sufficient activation. For the nanofiber membrane prepared according to Example 1 of the present invention, it was checked whether cell activation occurred after culturing immune cells that were not stimulated.

Example 8-1

Preparation of Bone Marrow-Derived Dendritic Cells and Peritoneal Macrophages Dendritic cells that were differentiated myeloid cells by cytokines were used. Bone marrow cells were isolated from the thighs and calves of 5 to 6 week old C57BL/6 mice. The isolated bone marrow cells ($1 \times 10^6$ cells/mL) were cultured using HEPES/RPMI-1640 medium containing fetal bovine serum (10%), penicillin (100 U/ml) and streptomycin (100

μg/ml) in an incubator at 37° C. supplied with 10% $CO_2$, and 20 ng/mL of granulocyte macrophage colony stimulating factor (GM-CSF) and 20 ng/mL of interleukin-4 (IL-4) were incubated together for 7 days to induce differentiation into dendritic cells. Differentiated dendritic cells were isolated using microbeads to which antibodies against CD11c, the specific protein surface factor of these cells are bound.

Mouse peritoneal cavity-derived cells were used for macrophage. 2 mL of 3% thioglycollate was injected into the mouse abdominal cavity and after 3 days, cells contained in the peritoneal solution were separated and $1 \times 10^5$ cells were incubated in 200 μL of RPMI-1640 culture solution (10% FBS, 100 IU/mL of penicillin and 100 μg/mL of streptomycin) in 96 well culture plates. Macrophages were isolated after 1 day of culture using microbeads to which F4/80 antibody was bound and washed twice with culture solution.

Example 8-2

Measurement of Culture and Activation of Dendritic Cells and Macrophages

The activation degree of dendritic cells and macrophages in 24 hours in PVA and RGD-NaOH-PVA was measured by the number of CD86-expressing cells on the surface of these cells. The cultured dendritic cells were reacted with CD11c antibody which allophycocyanin (APC) was bound to and CD86 antibody which fluorescein isothiocyanate (FITC) was bound to and peritoneal fluid-derived macrophages were reacted with F4/80 antibody which phycoerythrin (PE) was bound to and CD86 antibody which FITC was bound to and flow cytometry was measured (model MACSQuant, Mltenyi Biotec, USA). Activating cells were expressed as % of cells expressing CD86 in total response cells.

Figure 12:
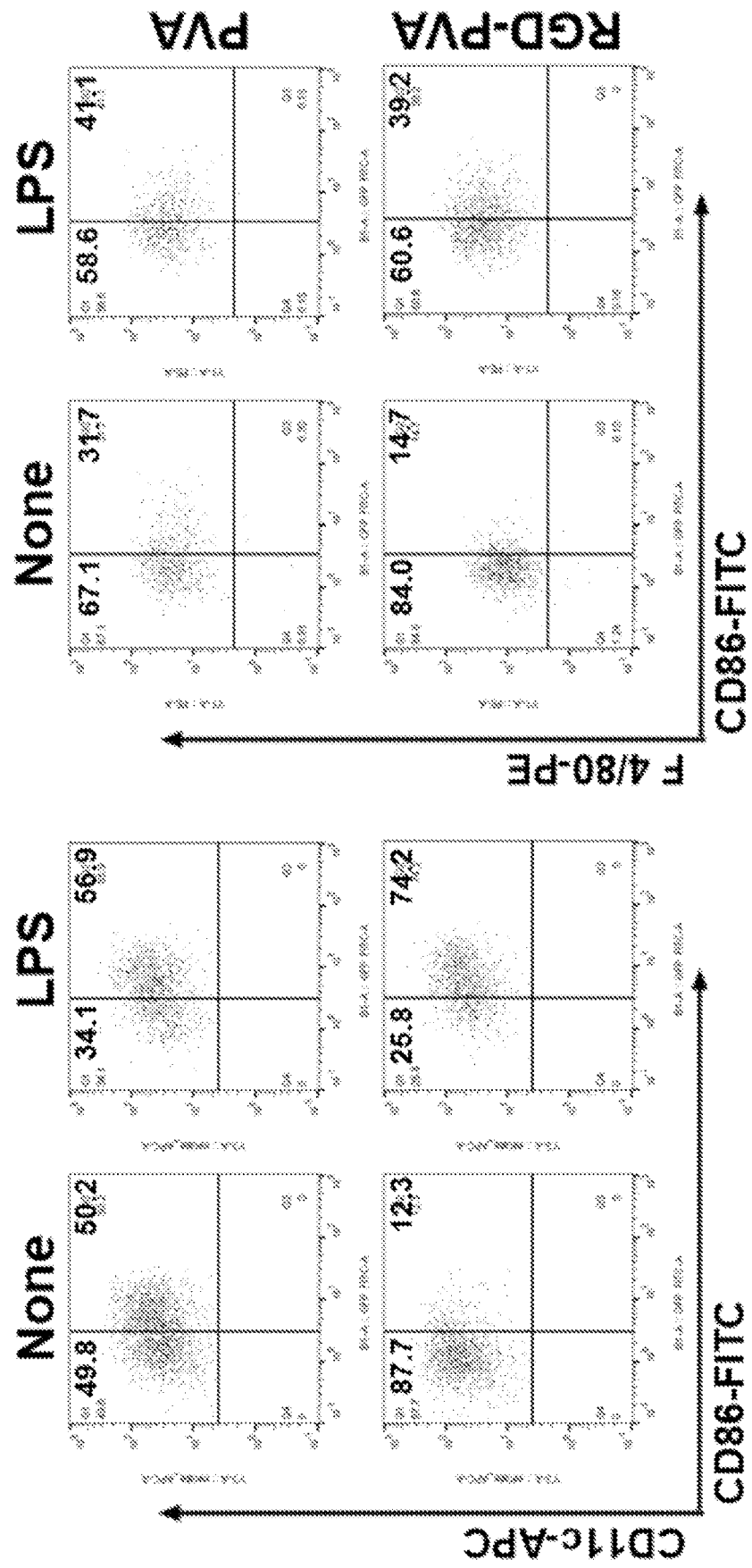
FIG. 12 shows a flow cytometry result of the expression degree of CD86 on the surface of these cells to analyze the activation level of CD11c+ dendritic cells and F4/80+ macrophages, which are immune cells cultured on a PVA membrane and RGD-PVA membrane treated with sodium hydroxide

As shown in FIG. 12, when CD11c$^+$ dendritic cells were cultured on the PVA membrane developed in the present invention, CD86-expressing cells, activation indicator, were markedly increased by 50% and the number of CD86-positive cells was 55% due to LPS stimulation and no further increase in CD86 expression was observed and thus it was confirmed that dendritic cells cultured in an unstimulated state exhibited self-activation. Dendritic cells cultured in RGD-NaOH-PVA showed very low CD86 expression of about 10% and increased by 75% when stimulated with LPS and dendritic cells cultured without stimulation are inactive and fully activated by stimulation. In addition, when the F4/80$^+$ macrophages were cultured on the PVA membrane, the percentage of CD86-positive cells was 30%, which was slightly lower than that of dendritic cells, but activation occurred. Macrophages cultured on the RGD-NaOH-PVA membrane did not activate and were shown to be activated by stimulation of LPS.

Figure 13:
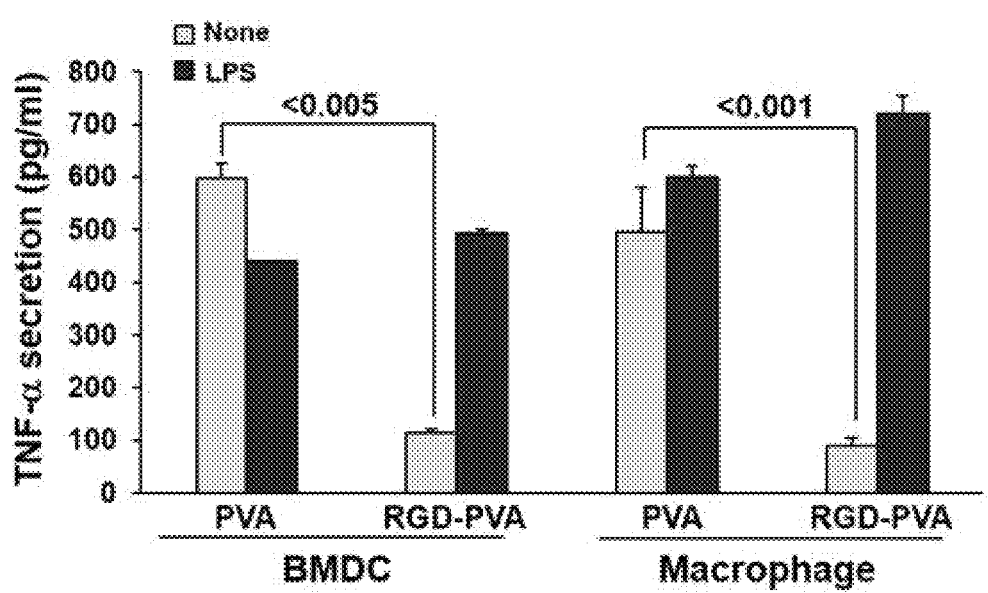
FIG. 13 shows results of comparing the activation level of dendritic cells (BMDC) and macrophages cultured on PVA membrane and RGD-PVA membrane treated with sodium hydroxide by measuring TNF-α secretion concentration by ELISA method.

The amount of tumor necrosis factor (TNF)-α secreted into the culture medium was measured in a state in which dendritic cells and macrophages were cultured in PVA and RGD-NaOH-PVA for 24 hours. As shown in FIG. 13, the amount of TNF-α secreted in the culture medium after 24 hours of dendritic cell culture was increased to about 700 pg/mL, and the amount of secretion was not increased when LPS was added. In comparison, when dendritic cells were incubated in RGD-NaOH-PVA, the amount of secreted TNF-α was measured below 100 pg/mL and it was increased to 500 pg/mL when stimulated with LPS. The secretion of TNF-α also exhibited similarly when peritoneal cavity-derived macrophages were cultured in PVA and RGD-NaOH-PVA. Therefore, the activation of immune cells when cultured in PVA nanofibers can be overcome by a method of preparing RGD-containing nanofibers.

Example 8-3

Observation of Morphology of Immune Cells Cultured in PVA and RGD-PVA by Scanning Electron Microscope The morphology of dendritic cells and macrophages attached to the PVA membrane on which the cells were cultured was confirmed by scanning electron microscopy. The cultured macrophages were firstly fixed at 4° C. for 24 hours with 0.1 M phosphate buffer containing 3% glutaraldehyde. After washing three times with phosphate buffer solution, they were fixed for 2 hours with 1% osmium tetraoxide. After dehydration by ethanol, the nanofibers were separated from the 8-well plate, attached to carbon tape, and coated with gold using an ion sputter coater. Gold-coated nanofibers were placed in a scanning electron microscope and subjected to vacuum to analyze the images.

Figure 14:
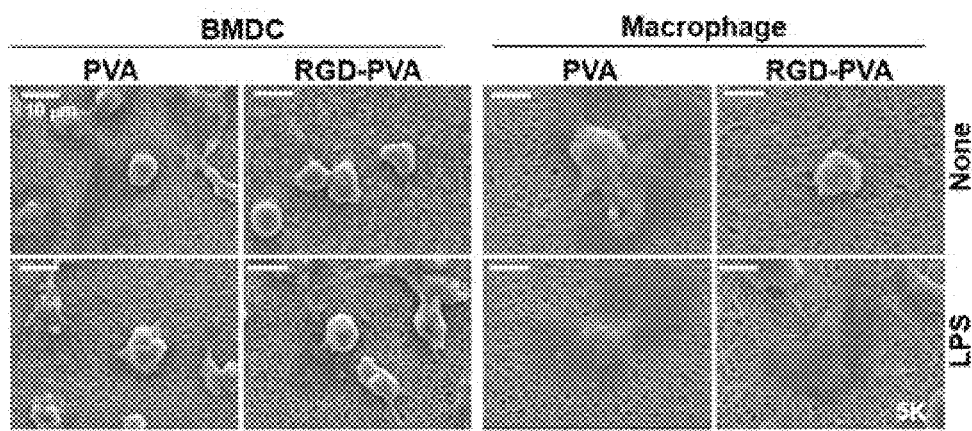
FIG. 14 shows a result of confirming the cell adhesion patterns by scanning electron microscopy to verify the activation of immune cells cultured on the PVA membrane and RGD-PVA membrane treated with sodium hydroxide.

Referring to FIG. 14, the dendritic cells and the macrophages attached to the PVA membrane had long and branching shape and the morphology of these cells did not show a significant difference when stimulated with LPS. The two types of cells cultured on the RGD-NaOH-PVA membrane were mainly round in shape and the cells were long and branching only when stimulated with LPS. These results suggest that the dendritic cells and the macrophages are activated in the PVA membrane and the PVA membrane including RGD is a support for providing cell stabilization.

Example 8-4

Figure 15:
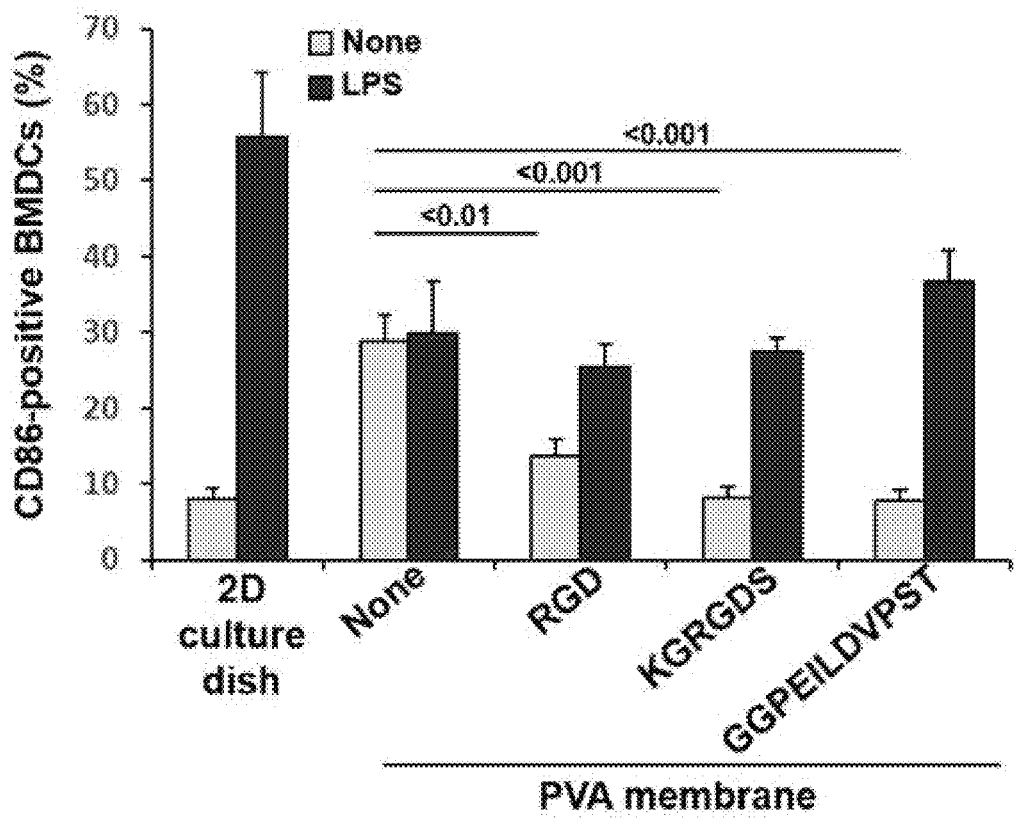
FIG. 15 shows a result of measuring CD86 expression of dendritic cells cultured on the PVA membranes containing the peptide KGRGDS and peptide GGPEILDVPST by flow cytometry after treating these membranes with sodium hydroxide.

Measurement of Activity of Immune Cells Cultured on Membrane Containing Cell Binding Peptide Other than RGD The activation of dendritic cells cultured on PVA membranes containing peptides KGRGDS and peptides GGPEILDVPST as well as RGD peptides containing PVA membranes was measured. Referring to FIG. 15, dendritic cells did not show activation without stimulation, and the expression of CD86 was significantly increased by LPS, indicating that the immune cells can be cultured in inactive form in the PVA membrane containing the peptide portion of fibronectin that binds to the integrin of the cell membrane.

Example 9

Figure 16:
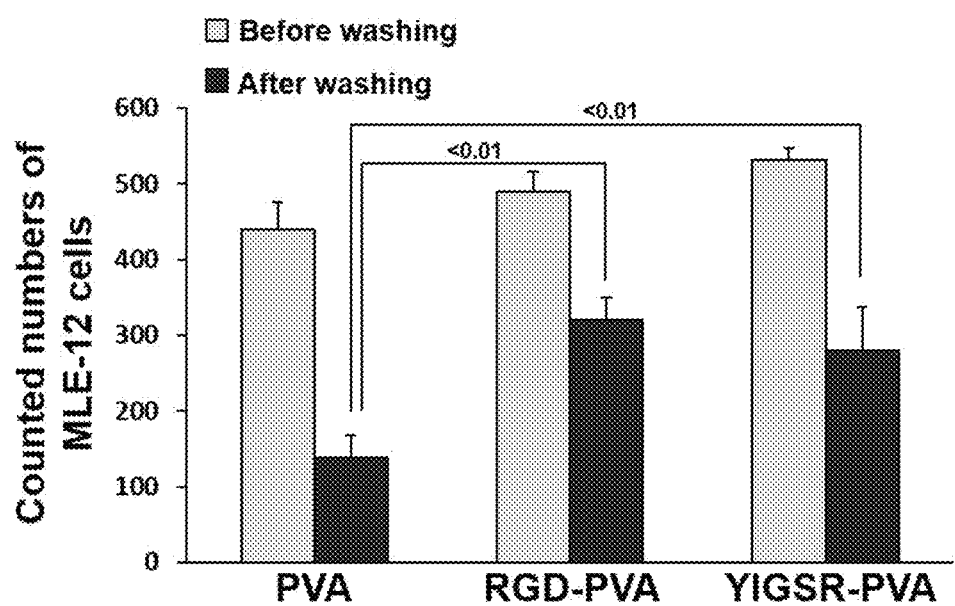
FIG. 16 shows a result of measuring the adhesion of airway epithelial MLE-12 cells cultured on the PVA membranes containing YIGSR, a peptide of the cell adhesion domain of the laminin protein after treating these membranes with sodium hydroxide, compared with the RGD-PVA membrane.
Figure 17:
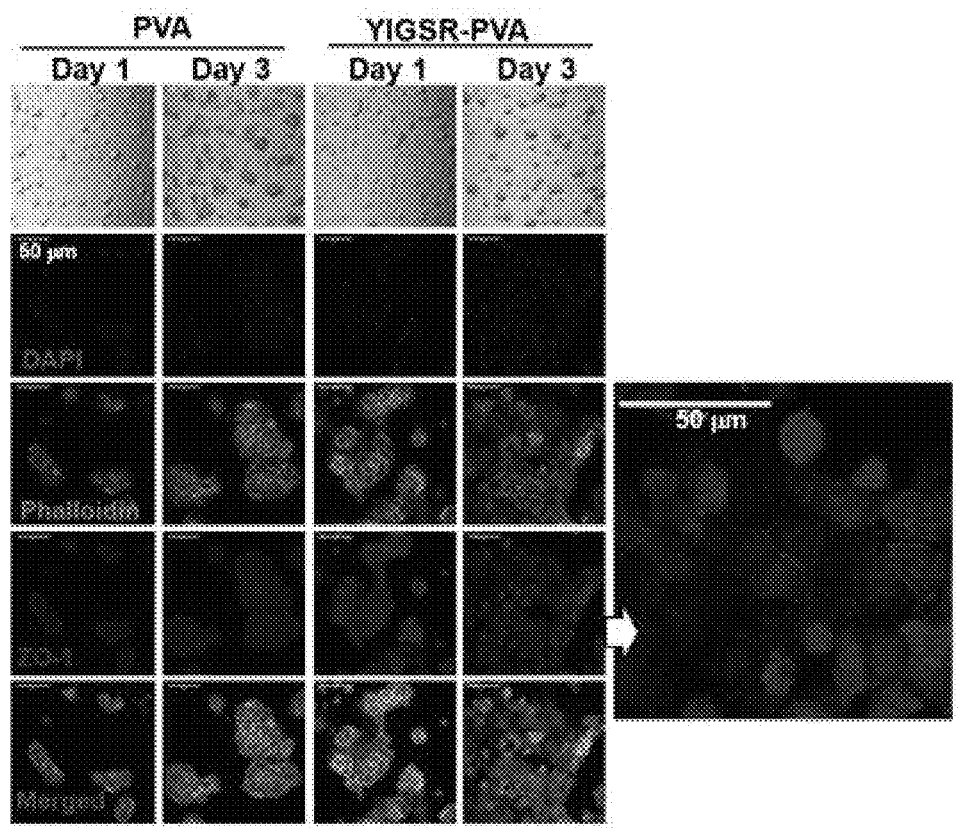
FIG. 17 shows a result of observing the morphology of airway epithelial MLE-12 cells cultured on the PVA membranes containing YIGSR, a peptide of the cell adhesion domain of the laminin protein after treating these membranes with sodium hydroxide by the confocal microscope.

Evaluation of Adhesion of Cells Cultured on YIGSR-PVA Membrane Treated with Sodium Hydroxide YIGSR is known as a peptide sequence involved in cell adhesion in laminin sequence, a protein of the basement membrane. Whether YIGSR-PVA membranes containing YIGSR peptide (50 μg/mL) in PVA can be used as a support with increased cell binding capacity was investigated. Airway epithelial cells attach to the basement membrane containing laminin in the tissue to constitute airway epithelial tissue. PVA membrane containing peptide YIGSR was prepared by electrospinning, treated with sodium hydroxide (hereinafter, YIGSR-NaOH-PVA membrane), and airway epithelial cells were cultured and the adhesion and morphology of the cells were observed by confocal microscopy. Referring to FIG. 16, when MLE-12 airway epithelial cells cultured on a YIGSR-NaOH-PVA membrane were washed with a culture medium and the number of attached cells was measured, the increase was greater than that cultured on a PVA membrane, and the number of cells was nearly same as the cells cultured on the RGD-NaOH-PVA membrane. As shown in FIG. 17, the airway epithelial cells cultured on the PVA membrane increased intercellular aggregation and in the RGD-NaOH-PVA membrane, the degree of agglomeration was slightly decreased, but a pattern of adhesion was observed. In comparison, airway epithelial cells cultured on the YIGSR-NaOH-PVA membrane showed almost no cell aggregation. The cells in the membrane adhered in a uniform distribution, and the enlarged image shows that the cells do not aggregate but the intercellular tight junction occurs well where the cells are in contact.

Figure 18:
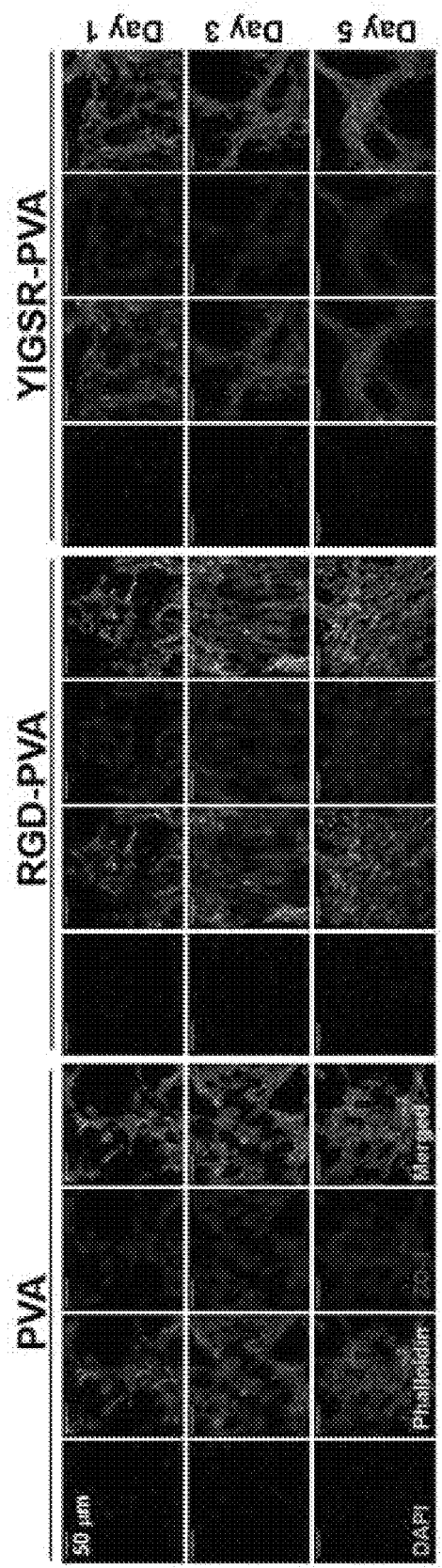
FIG. 18 shows a result of observing the proliferation state and cell junction of vascular endothelial cells cultured on the PVA membranes containing peptide YIGSR after treating these membranes with sodium hydroxide by the confocal microscope.

Vascular endothelial cells also attach to the basement membrane containing laminin in tissues. FIG. 18 shows the results of observing the culture state of bEND.3 cells, which are vascular endothelial cells, in YIGSR-NaOH-PVA membrane containing peptide YIGSR. bEND.3 cells were purchased from ATCC (ATCC® CRL-2299™) as vascular endothelial cells of brain tissue and cultured using Dulbecco's Modified Eagle's Medium (DMEM). Compared to cells cultured on the PVA membrane, cells cultured on the RGD-PVA membrane showed more spreading and binding. In comparison, bEND.3 cells, a vascular endothelial cell line cultured on the YIGSR-NaOH-PVA membrane, have a smaller cell size than the cells cultured on the RGD-NaOH-PVA membrane and the tight junction was clear and characteristically showed the appearance of tube formation.

Example 10

Measurement of Three-Dimensional Culture Characteristics of Primary Hepatocytes in RGD-Containing PVA Membrane Hepatocytes that perform the inherent function of the liver as epithelial cells of liver tissue bind integrin α5β1 expressed on the cell surface and collagen distributed in the space of disse of liver tissue through fibronectin attached to collagen. Since in two-dimensional culture, primary hepatocytes occur apoptosis within one to two days after culturing, and thus have limitations as a hepatocyte culture method, as a modified two-dimensional culture method, the sandwich method of seeding cells in a collagen-coated culture dish and then placing a matrigel on the cells and culturing them is most commonly used. Even if the sandwich method is used in hepatocyte culture, it should be cultured in a medium composition containing special medium such as William's E medium, dexamethasone, insulin, etc. and even if hepatocytes survive, the intrinsic biological and physiological activity and cell adhesion are remarkably degraded and has the disadvantage that long-term culture is impossible.

There is a three-dimensional culture method using a hydrogel to overcome the disadvantages of the two-dimensional culture of hepatocytes, but the hepatocytes cultured in the hydrogel form a spheroid and thus the monolayer form of epithelial cells in liver tissue is not achieved. Therefore, when using a PVA membrane, an RGD-PVA membrane containing RGD, and a RGD-NaOH-PVA membrane treated with NaOH as a support for overcoming the hepatocyte culture technology, the possibility of three-dimensional monolayer culture of primary hepatocytes was evaluated.

Example 10-1

Isolation and Culture Method of Primary Hepatocytes

Primary hepatocytes were used by isolating from liver tissue of C57BL/6 mice. After anesthetizing the mouse with ether, the abdomen and chest area were thoroughly washed with 70% ethanol and the lower abdomen was vertically dissected. After inserting a 24 G venous catheter into the hepatic portal vein, 60 mL of Hank's balanced salt solution (HBSS, 0.5 mM EDTA, 25 mM HEPES) filled in a syringe was flowed in an amount of 3 mL per minute using a syringe pump. After confirming that the liver was swollen, the inferior vena cava was cut and the speed of the pump was increased to 7-9 mL per minute. After flowing all HBSS, digestion buffer (50 mL) containing 15 mM HEPES, penicillin, and collagenase type IV (100 CDU/mL) into DMEM-low glucose was flowed at 7-9 mL/min. After carefully removing the syringe and the venous catheter, the liver was separated using forceps, and put into digestion buffer, and liver cells were obtained by dissolving the liver tissue with tweezers. After filtering the obtained hepatocytes with a strainer, the hepatocytes passed through were filled with a 30 mL of separation buffer composed of DMEM high glucose and DMEM F-12 (1:1), followed by centrifugal separation at 4° C. for 2 minutes at a speed of 50×g. This process was repeated three times, and the hepatocytes were diluted in separation buffer and dispensed to incubate the cells in an incubator maintained at 37° C. with a 5% $CO_2$ concentration. After 2 hours, the separation buffer was removed and DMEM-high glucose culture containing 10% fetal bovine serum and 1% penicillin was added.

Example 10-2

Figure 19:
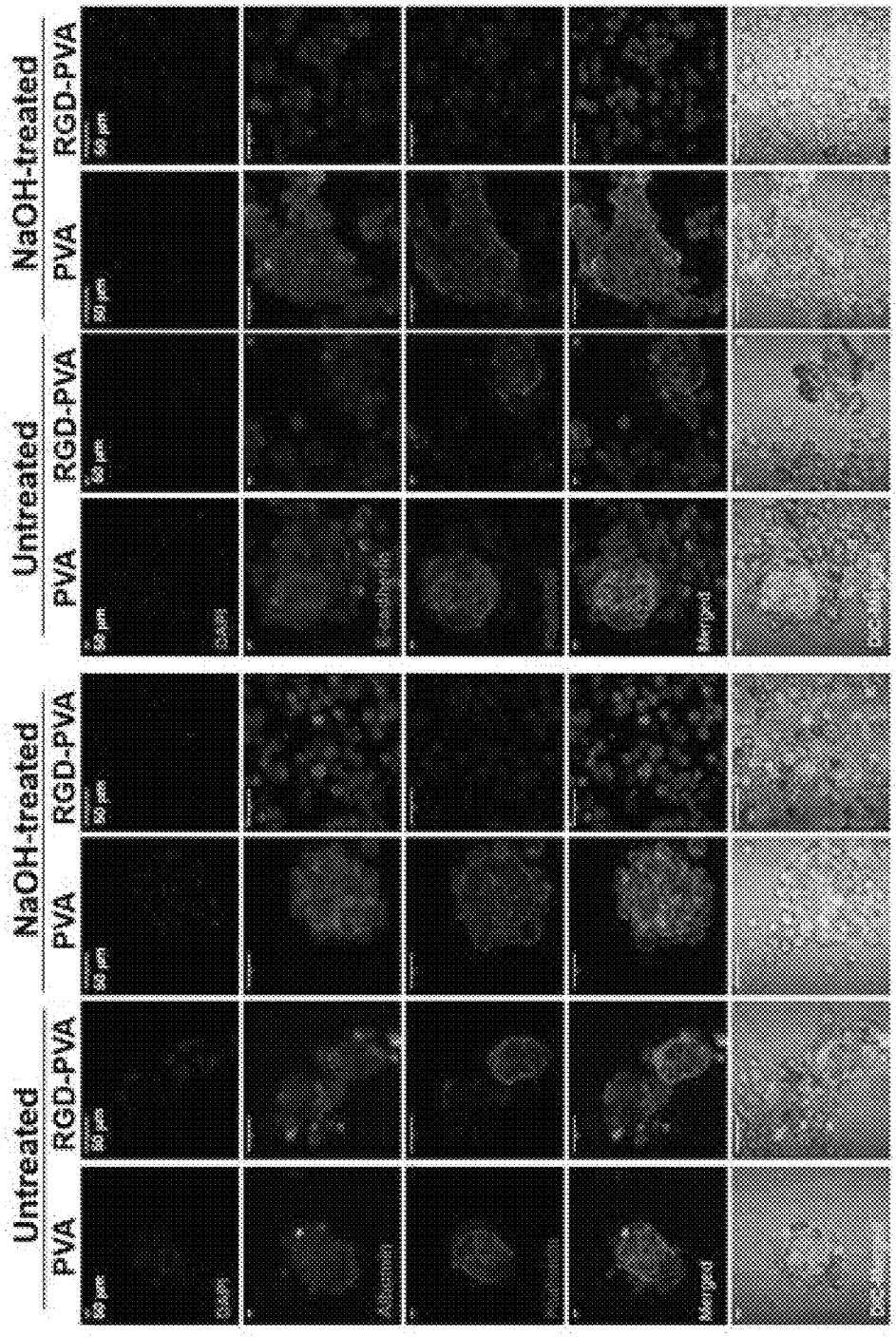
FIG. 19 shows a result of measuring the expression levels of albumin, E-cadherin and actin and the cell growth patterns of primary hepatocytes cultured for 7 days on untreated and sodium hydroxide-treated PVA and RGD-PVA membranes by the confocal microscope.

Long-Term Culture and Morphology of Hepatocytes in PVA Membrane Containing Fibronectin Peptide Treated with Sodium Hydroxide The morphology and spheroid formation of primary hepatocytes cultured for 7 days on a PVA membrane, an RGD-PVA membrane containing RGD, and an RGD-NaOH-PVA membrane treated with sodium hydroxide was measured by confocal microscopy. As shown in FIG. 19, when primary hepatocytes were cultured for 7 days on a PVA membrane and an RGD-PVA membrane untreated with sodium hydroxide, hepatocytes under both conditions aggregated with each other and formed spheroids of similar size. In addition, in these cases, extracellular actin was strongly expressed in spheroids showing cell aggregation. Although spheroid formation of hepatocytes was still observed in the PVA membrane treated with sodium hydroxide, the hepatocytes cultured on the RGD-NaOH-PVA membrane were attached to each cell in a uniform distribution with no cell aggregation. Even when the distribution of actin was measured by phalloidin staining, the extracellular actin shown in the spheroid was not expressed. The level of albumin expression in primary hepatocytes cultured for 7 days was fully detected in spheroid-forming or uniformly distributed cells. When fluorescein stained with E-cadherin, expression was detected at the site of intercellular contact, and rarely expressed at other sites of the cell, so that primary hepatocytes maintained their function in long-term culture and could be cultured as an ideal three-dimensional culture of single layer.

Figure 20:
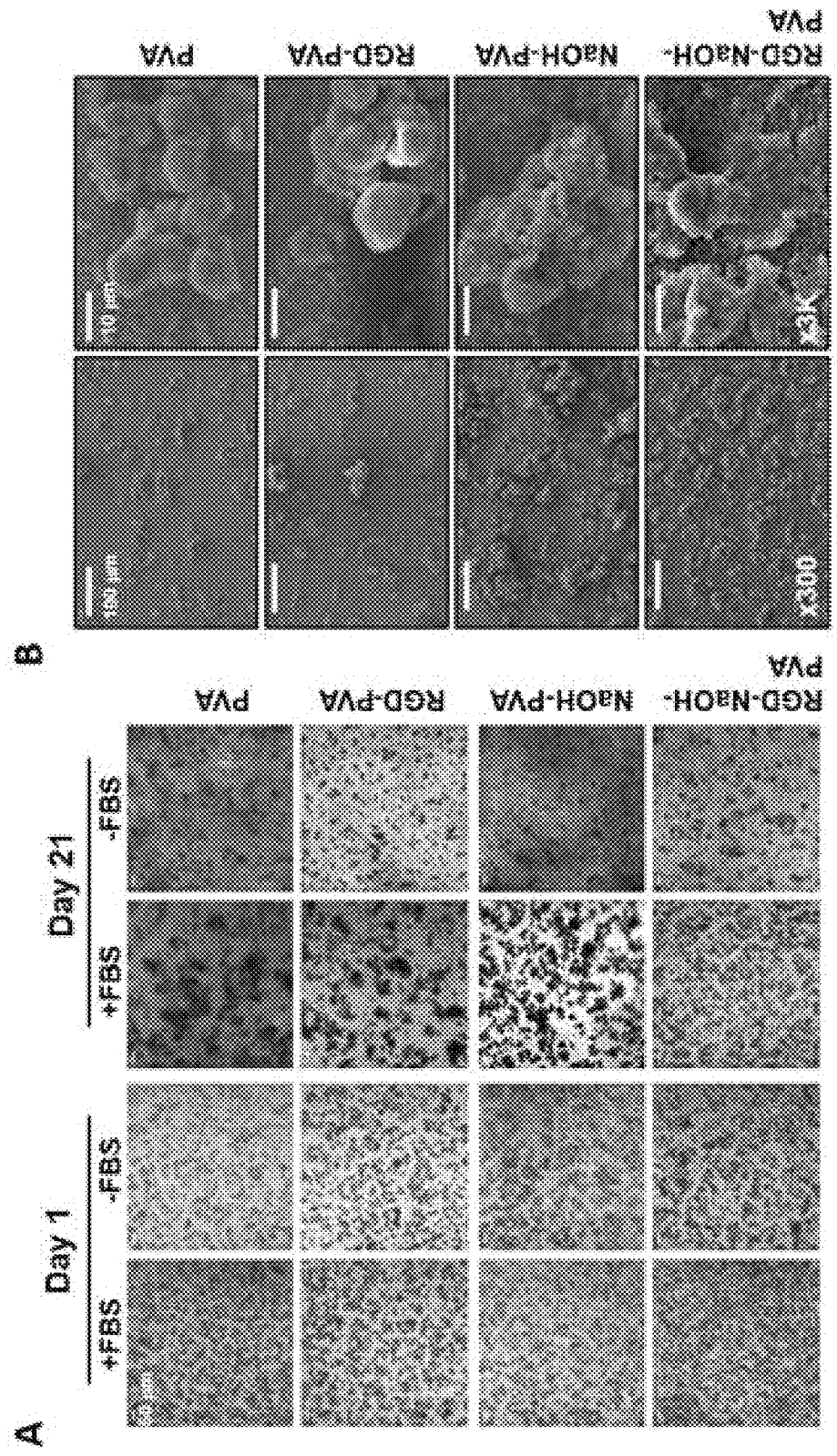
FIG. 20 shows results of observing primary hepatocytes cultured for 21 days on untreated and sodium hydroxide-treated PVA and RGD-PVA membranes by the differential interference microscope (FIG. 20A) and cell morphology by the electron microscope (FIG. 20B).

After 21 days of incubation on the RGD-NaOH-PVA membrane, the primary hepatocytes were examined for maintenance of their high survival rate, constant distribution and adhesion. Referring to the differential interference microscopic image shown in FIG. 20A, primary hepatocytes cultured on the RGD-NaOH-PVA membrane for up to 21 days were significantly reduced in the aggregation of the hepatocytes and like cells after 1 day of culture, the cells were uniformly distributed on the surface of the culture dish and cell adhesion was increased. Each cell was found to be uniformly distributed and cell adhesion was increased. When serum was not added to primary hepatocytes cultured on PVA membrane, spheroid formation tended to decrease as the number of cells decreased, but when serum was added to primary hepatocytes cultured on RGD-NaOH-PVA membrane, the number of cells increased than the case without serum, but spheroid formation did not occur. In particular, most of the cells cultured on the RGD-NaOH-PVA membrane, as shown in the electron microscope image of FIG. 20B, are scattered alone and distributed in a regular size and cell morphology, unlike the cell aggregation phenomenon shown in the membrane without sodium hydroxide.

Figure 21:
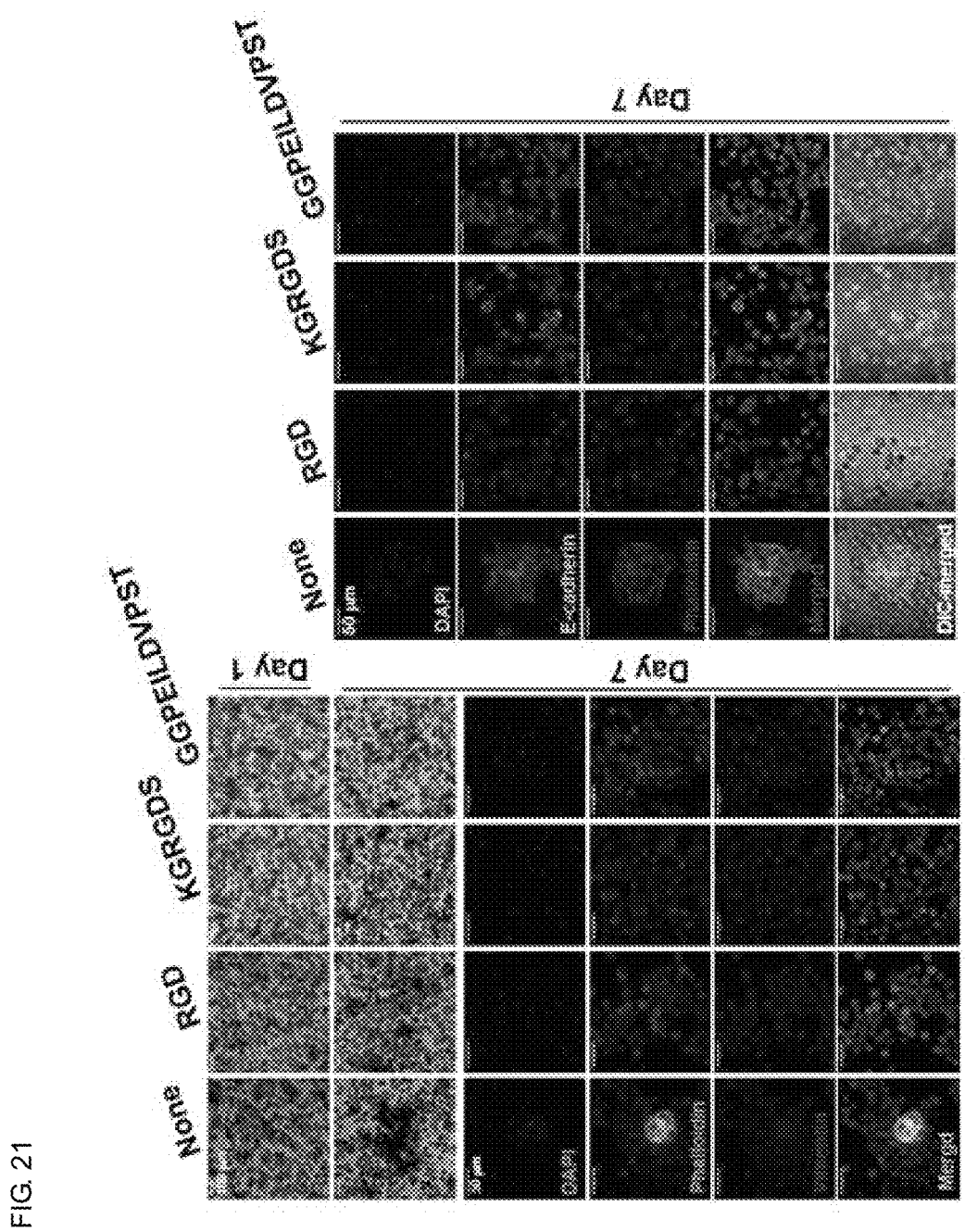
FIG. 21 shows a result of measuring vimentin and E-cadherin expression of primary hepatocytes cultured on PVA membranes containing peptides KGRGDS and peptides GGPEILDVPST after treating these membranes with sodium hydroxide by the confocal microscope.

Referring to FIG. 21, when the primary hepatocytes were cultured on the PVA membrane containing KGRGDS and GGPEILDVPST for 7 days, the adhesion and distribution of the cells were further improved when the morphology of the primary hepatocytes was compared with that on the RGD-NaOH-PVA membrane. In particular, when cultured on a membrane containing these peptides, cell aggregation hardly occurred, and phalloidin staining was uniform throughout the cells. E-cadherin expression was detected in primary hepatocytes cultured on membranes containing these peptides and there was no increase in vimentin expression as in mesenchymal-derived cells and thus it is confirmed that epithelial-mesenchymal transition does not appear to occur.

Example 11

Cell Culture and Characterization in Fucoidan-Containing PVA Nanofibers

Fucoidan has a structure similar to proteoglycan in the extracellular matrix and is known to bind to selectin expressed on the cell surface. It is reported that the cell adhesion ability is enhanced when the hydrophilic fucoidan is prepared so as to uniformly contain in the hydrophobic polycaprolactone nanofibers. It is difficult to mix hydrophilic fucoidan and a polymer such as hydrophobic PCL in nanofiber as a homogeneous mixed form and to prepare the nanofiber uniformly. In order to solve the above problems of the prior art, it was investigated whether the fucoidan-containing nanofiber membrane could be provided as a PVA membrane with improved cell culture and adhesion.

Example 11-1

Fabrication of Fucoidan-Containing Nanofibers and Fucoidan Detection Method

Figure 22:
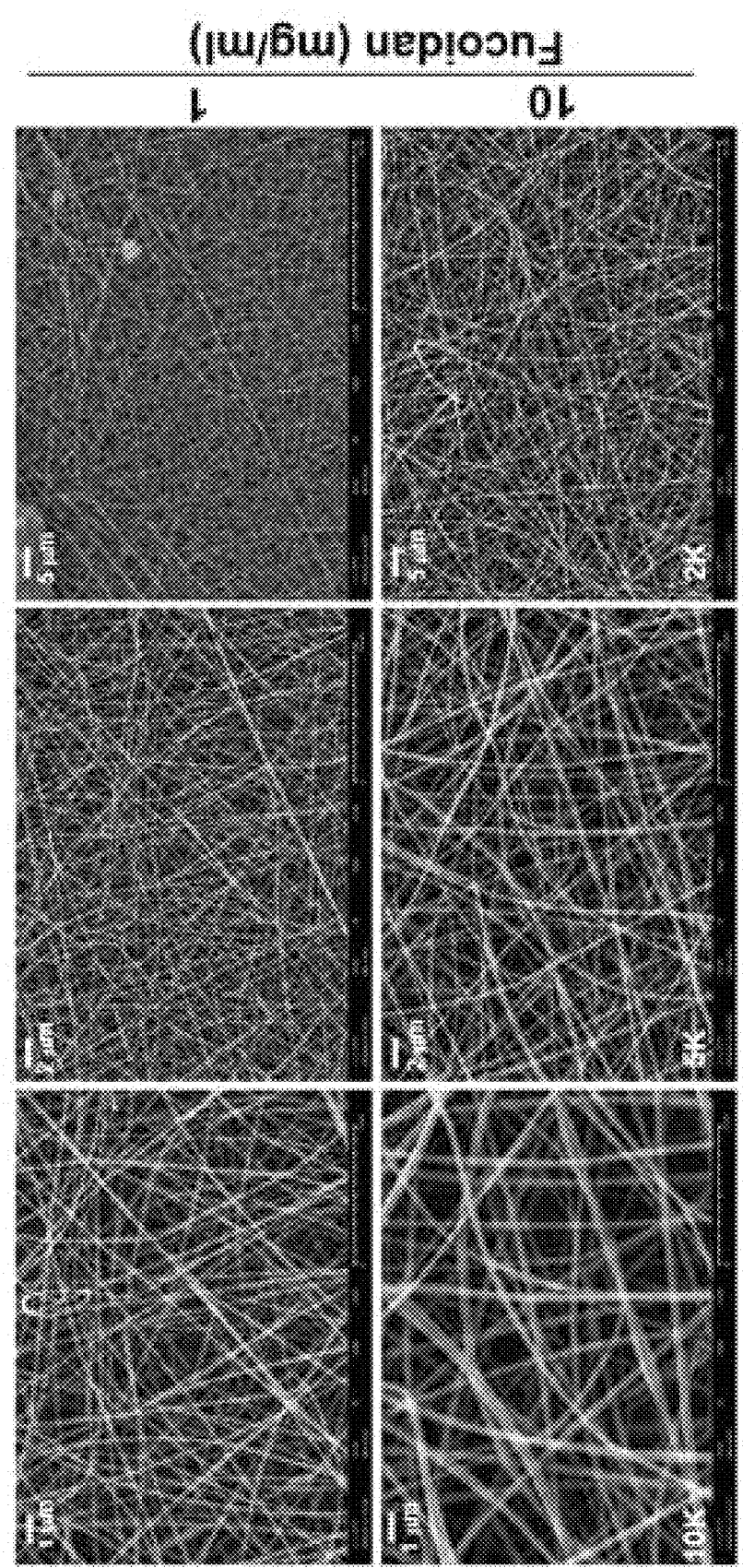
FIG. 22 shows an electron microscope image of confirming the shape and porosity of nanofibers after preparing fucoidan-PVA nanofibers containing fucoidan in PVA nanofibers by electrospinning.

A PVA membrane containing fucoidan, a polymer particle having a molecular weight of about 110 kDa, as well as a peptide that enhances cell binding ability to PVA (hereinafter, fucoidan-PVA membrane) was produced by electrospinning and was measured if nanofibers with uniform structure were prepared. It was measured whether or not produced. As shown in scanning electron microscope image shown in FIG. 22, fucoidan-PVA nanofibers were uniform in diameter and uniform in porosity even though they contained fucoidan as in PVA nanofibers. When the concentration of fucoidan was 10 mg/ml, the diameter of the nanofibers was slightly increased, but uniform diameters and voids were maintained.

Figure 23:
FIG. 23 shows a methylene blue staining image for detecting fucoidan in a PVA nanofiber membrane containing fucoidan (fucoidan-PVA).

In order to detect whether fucoidan is contained in fucoidan-PVA membrane, nanofibers were treated with methylene blue to examine whether fucoidan reacted and the membrane was stained. FIG. 23 shows methylene blue staining results for detecting fucoidan contained in a fucoidan-PVA membrane at a concentration of 1 mg/mL fucoidan. When the nanofiber membrane was immersed in a solvent containing 0.1% methylene blue (50 mM HCl/MetOH:acetone:$H_2O$ (6:4:15)), stained at room temperature for 10 minutes, washed three times for 5 minutes with distilled water and methylene blue on nanofibers was washed away, the PVA nanofibers did not show blue color, but fucoidan-PVA was shown to be dark blue. When methylene blue bound to fucoidan was decolored by destaining at room temperature for 20 minutes with a decolorizing reagent (5% acetic acid, 6% MetOH, 4% acetone) and drying and staining with methylene blue again, and even if the blue color of fucoidan-PVA nanofibers disappears due to destaining and are dyed again, from being dyed blue. Thus, fucoidan in PVA nanofibers containing fucoidan produced by electrospinning was shown to be continuously bound.

Figure 24:
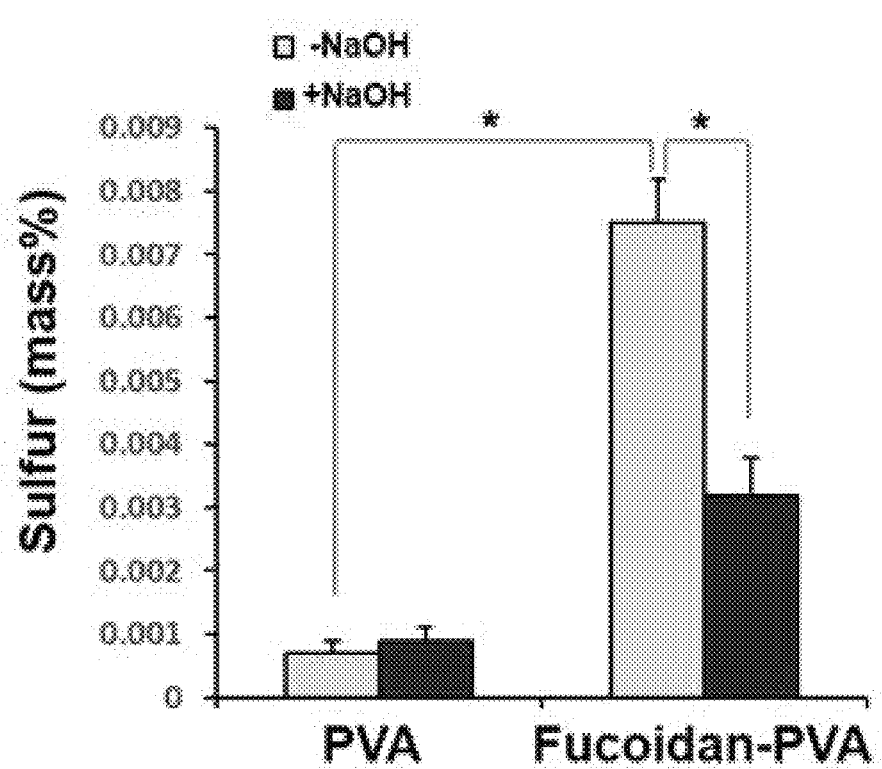
FIG. 24 shows a result of measuring sulfur element concentration constituting fucoidan to measure the remaining amount of fucoidan contained in fucoidan-PVA membrane after treating this membrane with sodium hydroxide and being released from nanofibers by wavelength dispersive X-ray fluorescence.

Since fucoidan contains fucose-sulfate as a specific component, it is possible to infer fucoidan content by quantitatively analyzing these components in the prepared nanofibers. Fucoidan contained in the fucoidan-PVA membrane was released after treatment of the nanofiber membrane with sodium hydroxide to determine the elemental concentration of sulfur remaining in the nanofibers by Wavelength Dispersive X-ray fluorescence (WD-XRF) as the concentration of sulfur in the total polymer (%). Referring to the results of FIG. 24, in the fucoidan-PVA membrane, the elemental concentration of sulfur was significantly increased in comparison with the control PVA membrane, and after the membrane was treated with sodium hydroxide, the concentration was significantly decreased, but it is higher than PVA treated with sodium hydroxide, indicating that fucoidan remains in the nanofibers.

Example 11-2

Measurement of Adhesion Capacity of Cells Cultured on Fucoidan-PVA Membrane

Figure 25:
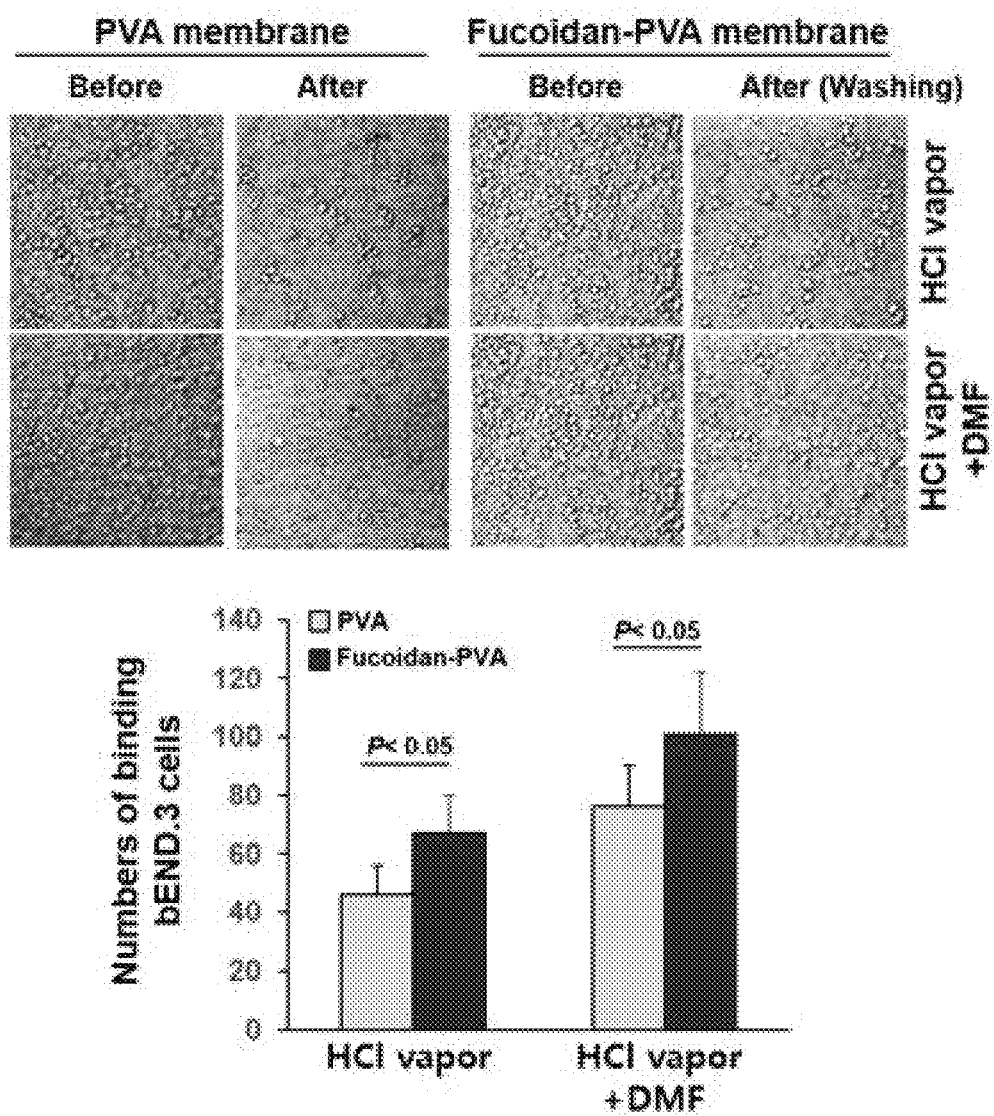
FIG. 25 shows a differential microscope image observing whether the adhesion of vascular endothelial cells cultured on fucoidan-PVA membrane is increased and the results of measuring the number of cells.

When the PVA and fucoidan-PVA membranes were treated with hydrochloric acid and dimethylformamide, and then treated with 1M sodium hydroxide for 12 hours and used for cell culture, it was examined whether there was a difference in cell adhesion on these membranes and there was an effect on cell adhesion containing fucoidan. Referring to FIG. 25, the PVA membrane or fucoidan-PVA membrane treated with hydrochloric acid vapor and dimethylformamide had higher adhesion number of bEND.3 vascular endothelial cells after washing with the culture medium than that treated with hydrochloric acid vapor only. Characteristically, in the case of only hydrochloric acid vapor treatment or hydrochloric acid vapor and DMF treatment, adhesion capability of cells cultured in fucoidan-PVA membrane was more increased than that in PVA membrane. Therefore, PVA nanofiber membranes containing fucoidan with improved cell adhesion can be prepared.

Example 11-3

Figure 26:
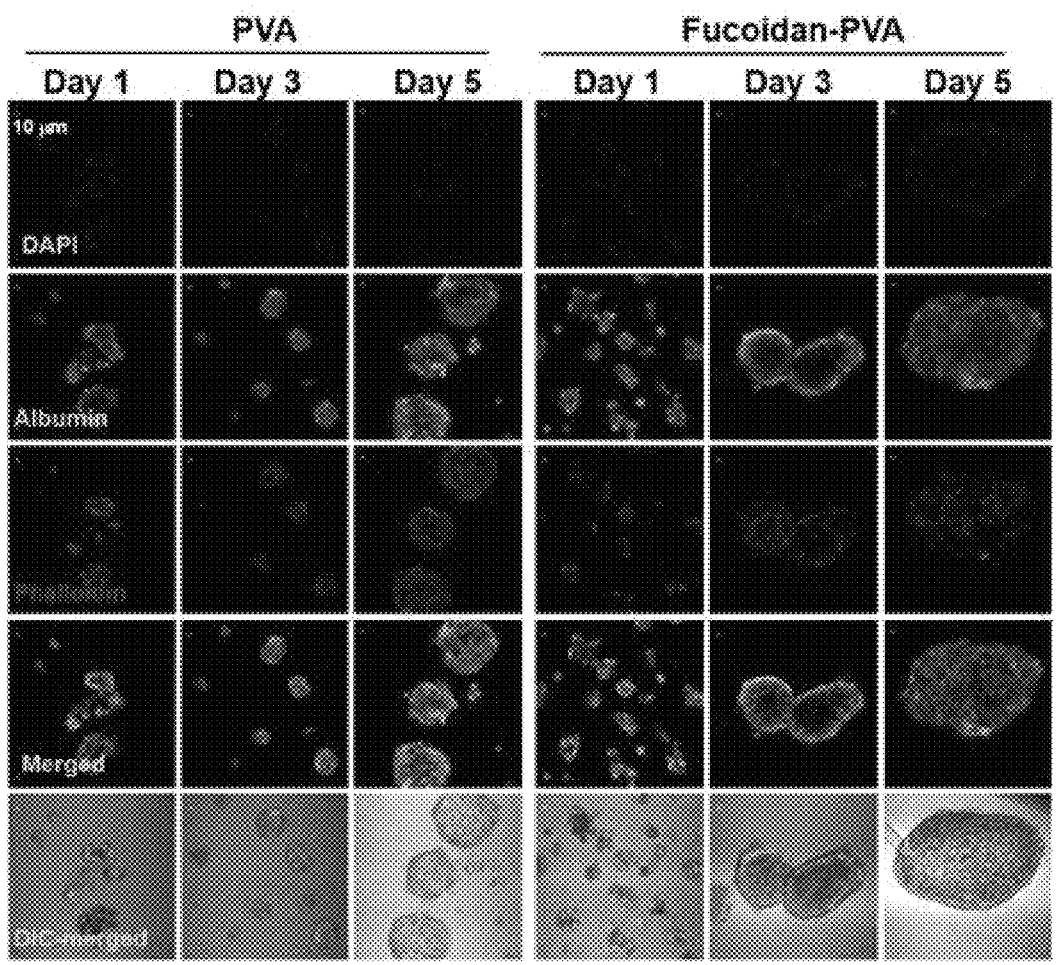
FIG. 26 shows a result of measuring spheroid formation, albumin expression, actin expression and distribution of primary hepatocytes cultured for 7 days on PVA and fucoidan-PVA membranes by the confocal microscope.

Long-Term Culture of Primary Hepatocytes in Fucoidan-Containing PVA Membrane Fucoidan released in the culture from fucoidan-PVA membrane may affect the cell adhesion and growth. Therefore, the long-term culture of primary hepatocytes in the fucoidan-PVA membrane treated with or without sodium hydroxide was performed to compare their adhesion patterns and growth. FIG. 26 shows the results of measuring the degree of spheroid formation of primary hepatocytes prepared for 7 days on fucoidan-PVA membranes prepared with nanofibers containing fucoidan and not treated with sodium hydroxide. Fucoidan was released from the PVA nanofibers containing fucoidan, which prevented the adhesion of cells to the membrane, thereby inducing the aggregation of primary hepatocytes, which increased more than suppressing spheroid formation. However, the expression of albumin is continuously maintained in hepatocytes forming spheroids, and thus it can be seen that the cell adhesion to membrane is decreased while the intercellular adhesion is increased and the cell function is maintained.

Figure 27:
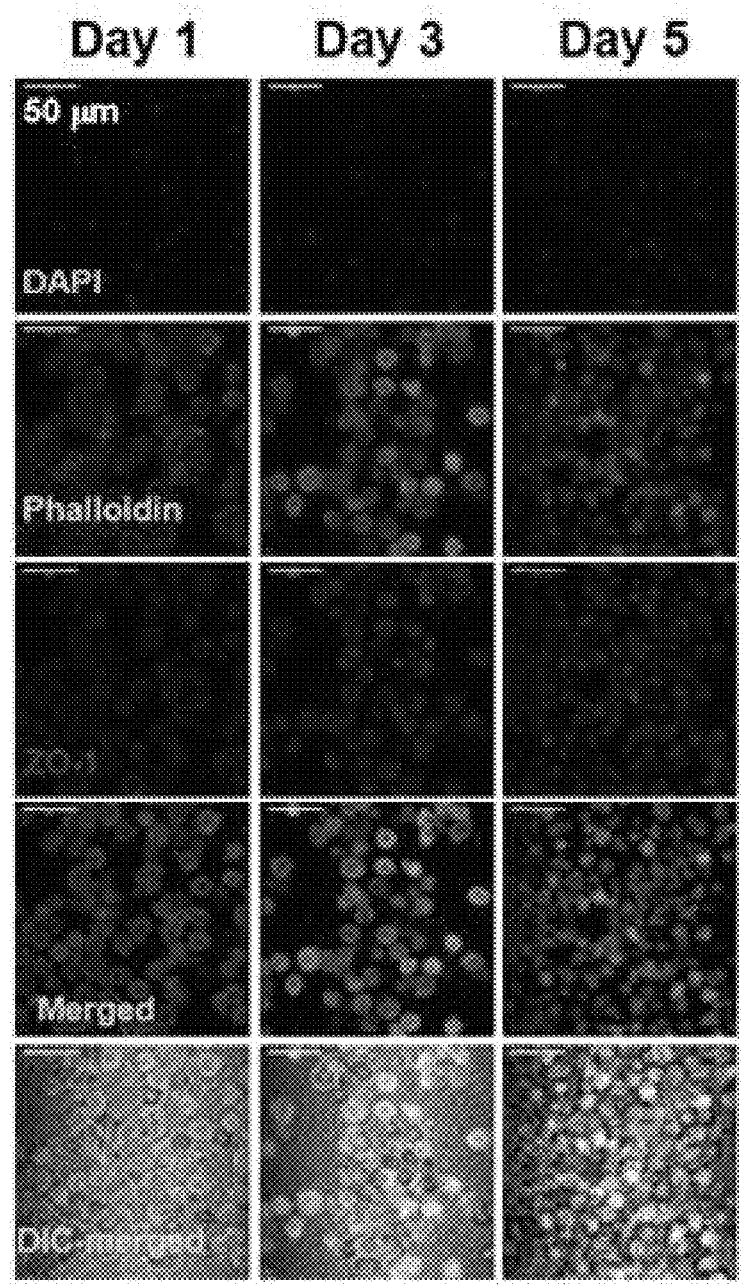
FIG. 27 is a confocal microscope image for examining the adhesion and distribution of primary hepatocytes cultured for 5 days on a fucoidan-PVA membrane treated with sodium hydroxide.

Referring to the image of FIG. 27 in which cell growth patterns was observed by confocal microscopy when culturing primary hepatocytes using a fucoidan-PVA membrane treated with sodium hydroxide for 5 days, primary hepatocytes cultured on fucoidan-PVA membrane treated with sodium hydroxide show increased adhesion and single cell adhesion and no spheroid formation due to cell aggregation, which is similar to the hepatocytes cultured in RGD-NaOH-PVA which are uniformly distributed and adhered to the membrane surface, Therefore, the fucoidan-containing PVA membrane, which is a natural product, as well as a cell adhesion peptide, can be prepared as a support for monolayer culture of primary hepatocytes.

Example 12

Evaluation of Effect of Radiation on Adhesion of Cell Cultured on PVA Membrane To date, the efficacy of anticancer drugs and radiation on the growth of cancer cells is mainly achieved in two dimensional culture conditions and especially, cell adhesion may affect the drug efficacy of these cells, but the culture conditions to exclude these factors have not been established, which may also be a reason for the limitations of proper support development. Therefore, the effect of radiation on the adhesion and growth of cells cultured in culture dish and PVA membrane was compared.

Figure 28:
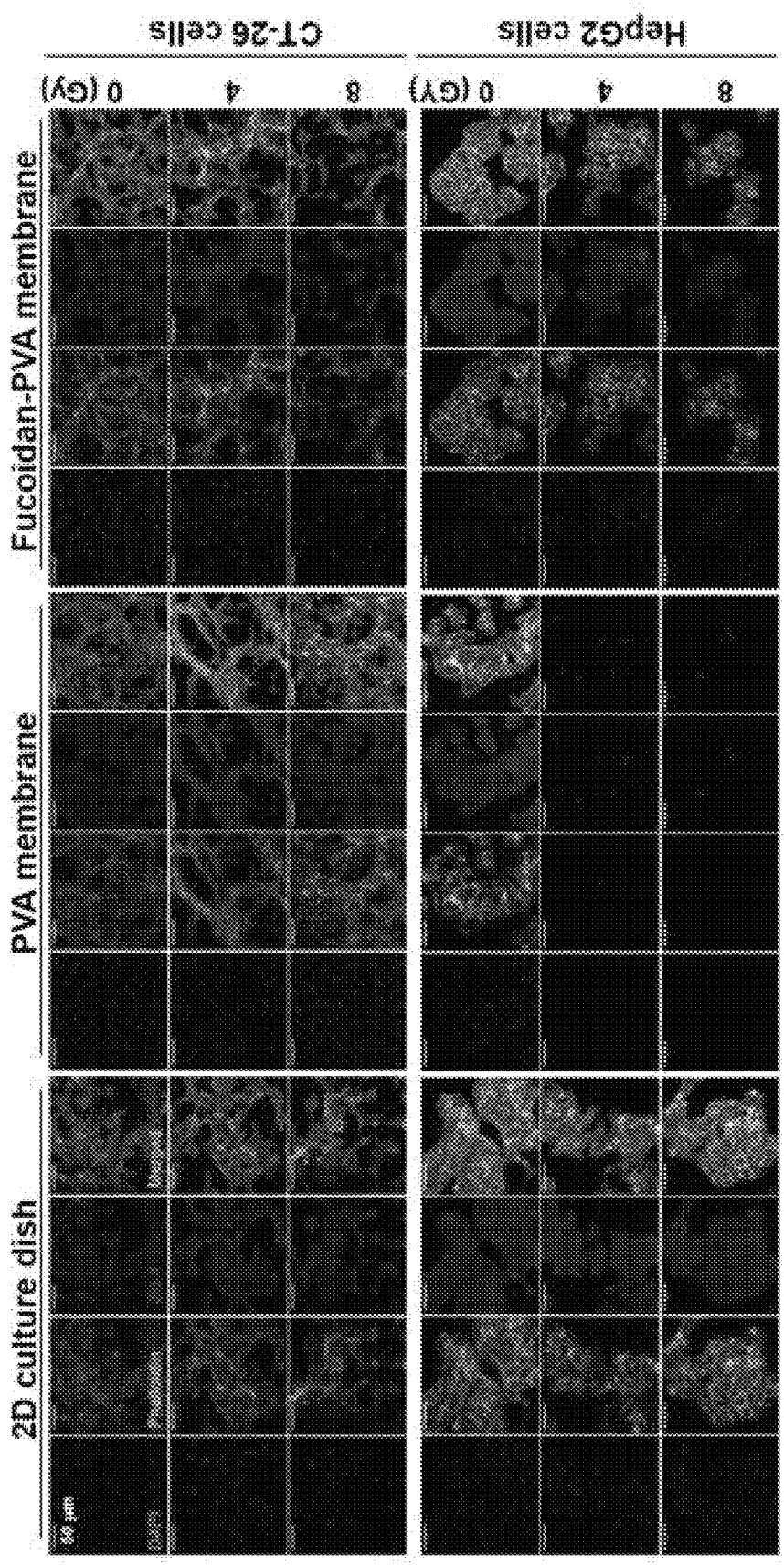
FIG. 28 is a confocal microscope image of measuring changes in the adhesion and the growth of irradiated cells in culture dishes and PVA membranes having different culture conditions.

The image of FIG. 28 shows the result of observing cell morphology, while CT26 colon cancer cells ($3\times10^4$/700 $\mu$L/cm$^2$) were dispensed on a culture dish and a PVA membrane, cultured for 2 days, and then irradiated with 4 Gy and 8 Gy, followed by culturing the cells for 2 days. CT26 cancer cells cultured in the culture dish were not significantly affected by the irradiation, however, cancer cells cultured on the PVA membrane showed decreased cell adhesion after 4 Gy treatment and increased expression of ZO-1 around the cells due to intercellular adhesion and after 8 Gy treatment, the cell was more round in shape and the intercellular tight junction was noticeable. When CT26 cells were cultured on fucoidan-PVA membrane and then irradiated with 4 Gy radiation, the adhesion of cells was maintained, compared to the cells cultured on the PVA membrane and the intercellular tight junction appeared to some extent, thereby having an effect of enhancing cell adhesion. However, the radiation at the high radiation dose of 8 Gy significantly reduced the number of cultured cells, which is not clear whether cancer cells bound to fucoidan are lost or cell death occurs due to poor adhesion.

HepG2 hepatocarcinoma cells were cultured for 2 days, and then irradiated with radiation at 4 Gy and 8 Gy, and the cells were cultured again for 2 days to observe the cell morphology in the similar manner as the above experiment. HepG2 cells cultured in culture dishes survive on the surface but showed characteristic intercellular aggregation. Irradiation showed no effect on cell adhesion or intercellular aggregation and did not significantly change the expression of ZO-1 involved in cell tight junction. Hepatocarcinoma cells cultured on PVA membrane showed a significant decrease in the number of cells after 2 days of irradiation at 4 Gy, resulting in defects of cell death or cell adhesion. When HepG2 hepatocarcinoma cells were cultured on fucoidan-PVA membrane and irradiated with radiation at 4 Gy, the number of attached cells was significantly lower than that of unradiated cells, but significantly lower than cells cultured on PVA membrane. The number of cells decreased compared with 4 Gy of radiation even when irradiated with 8 Gy of radiation, but a significant number of cells were observed compared to the cells cultured on the PVA membrane. In particular, the expression of ZO-1 involved in cell tight junction was found to be decreased by irradiation. Therefore, PVA membrane and cell adhesion factor-containing PVA membrane can be prepared and used as a three dimensional culture support that can compare and analyze the effect of radiation on cancer cells.

The present invention relates to a method of preparing a PVA nanofiber membrane comprising a substance capable of controlling cell-specific adhesion and can prepare nanofiber structures in which the hydrophilicity of the nanofibers can be secured while maintaining the inherent adhesion of the cells. In particular, the nanofiber structure produced by this method is not a simple technique of coating various kinds of materials for regulating cell adhesion, but it has an advantage that it can culture by blending in nanofibers to secrete adhesive materials or acting only on receptors on the cell surface.

While the present invention has been particularly described with reference to specific embodiments thereof, it is apparent that this specific description is only a preferred embodiment and that the scope of the present invention is not limited thereby to those skilled in the art. That is, the practical scope of the present invention is defined by the appended claims and their equivalents.

What is claimed is:

1. A method of preparing polyvinyl alcohol nanofiber membrane having enhanced cell adhesion, comprising:
   (1) preparing polyvinyl alcohol nanofiber membrane by adding cell-adhesive material to an electrospinning solution containing polyvinyl alcohol (PVA), polyacrylic acid (PAA) and glutaraldehyde (GA) and electrospinning;
   (2) cross-linking the polyvinyl alcohol nanofiber membrane by hydrochloric acid (HCl) vapor treatment, followed by crystallization by treating with dimethylformamide (DMF) solvent; and
   (3) treating crystallized polyvinyl alcohol nanofiber membrane with sodium hydroxide.

2. The method of preparing polyvinyl alcohol nanofiber membrane having enhanced cell adhesion of claim 1, wherein the cell-adhesive material is a cell-binding peptide or fucoidan.

3. The method of preparing polyvinyl alcohol nanofiber membrane having enhanced cell adhesion of claim 2, wherein the cell-binding peptide is any one or more peptides selected from the group consisting of RGD peptides, KGRGDS peptides, GGPEILDVPST peptides and YIGSR peptides.

4. The method of preparing polyvinyl alcohol nanofiber membrane having enhanced cell adhesion of claim 2, wherein the cell-binding peptide is added at a concentration of 10 to 300 μg/mL.

5. The method of preparing polyvinyl alcohol nanofiber membrane having enhanced cell adhesion of claim 2, wherein the fucoidan is added at a concentration of 1 to 20 mg/mL.

6. The method of preparing polyvinyl alcohol nanofiber membrane having enhanced cell adhesion of claim 1, wherein the cell is epithelial cells, vascular epithelial cells, cancer cells, fibroblasts, hepatocytes, immune cells or stromal cells.

\* \* \* \* \*